(12) United States Patent
Brabetz

(10) Patent No.: US 10,669,573 B2
(45) Date of Patent: Jun. 2, 2020

(54) CONFIRMATION TEST FOR PRIMARY NUCLEIC ACID AMPLIFICATION PRODUCTS IN A CONTINUOUS REACTION SETUP AND IMMEDIATE ANALYSIS VIA IMMUNOCHROMATOGRAPHIC METHODS

(71) Applicant: Biotype GmbH, Dresden (DE)

(72) Inventor: Werner Brabetz, Dresden (DE)

(73) Assignee: Biotype GmbH, Dresden (DE)

( * ) Notice: Subject to any disclaimer, the term of this patent is extended or adjusted under 35 U.S.C. 154(b) by 0 days.

(21) Appl. No.: 15/760,836

(22) PCT Filed: Sep. 15, 2016

(86) PCT No.: PCT/EP2016/071746
§ 371 (c)(1),
(2) Date: Mar. 16, 2018

(87) PCT Pub. No.: WO2017/046191
PCT Pub. Date: Mar. 23, 2017

(65) Prior Publication Data
US 2018/0363040 A1    Dec. 20, 2018

(30) Foreign Application Priority Data
Sep. 18, 2015    (DE) ........................ 10 2015 115 836

(51) Int. Cl.
| | | |
|---|---|---|
| *C12Q 1/68* | (2018.01) | |
| *C12Q 1/6844* | (2018.01) | |
| *C12Q 1/6853* | (2018.01) | |
| *C12Q 1/6823* | (2018.01) | |
| *C12Q 1/6851* | (2018.01) | |

(52) U.S. Cl.
CPC ......... *C12Q 1/6844* (2013.01); *C12Q 1/6823* (2013.01); *C12Q 1/6851* (2013.01); *C12Q 1/6853* (2013.01)

(58) Field of Classification Search
None
See application file for complete search history.

(56) References Cited

U.S. PATENT DOCUMENTS
2014/0087382 A1    3/2014    Allawi et al.

FOREIGN PATENT DOCUMENTS

| EP | 2 208 795 | 7/2010 |
|---|---|---|
| WO | WO 2008/083261 | 7/2008 |
| WO | WO 2009/117327 | 9/2009 |
| WO | WO 2009/155271 | 12/2009 |
| WO | WO 2012/067831 | 5/2012 |
| WO | WO 2015/024948 | 2/2015 |

OTHER PUBLICATIONS

Ahern, The Scientist 9 (15), 20 (1995).*
Kamphee et al. (2015) Rapid Molecular Detection of Multidrug-Resistant Tuberculosis by PCR-Nucleic Acid Lateral Flow Immunoassay. PLOS ONE. 10(9):1-17.
Hosono et al. (2007) Multiplex PCR-Based Real-Time Invader Assay (mPCR-RETINA): A Novel SNP-Based Method for Detecting Allelic Asymmetries Within Copy Number Variation Regions. Human Mutation 29(1):182-189.
International Search Report corresponding to International Application No. PCT/EP2016/071746 dated Jan. 10, 2017.
Mehlig et al. (2014) DNA-probe based detection for differential diagnosis of dermatomycoses. Mycoses 57:42-43.
Office Action corresponding to German Patent Application No. 10 2015 115 836.1, dated Feb. 4, 2016.

* cited by examiner

*Primary Examiner* — James Martinell
(74) *Attorney, Agent, or Firm* — Jenkins, Wilson, Taylor & Hunt, P.A.

(57) ABSTRACT

The invention relates to a method for confirming an amplified nucleic acid target sequence (target sequence), preferably from human samples, during a multiplication reaction in a collective and continuous reaction batch as a one-pot process, wherein the confirmation of the target sequence amplification product is obtained by means of a hapten-pair-marked artificial template amplification product. The artificial template sequence is amplified and optionally marked by means of the 5'-cleavage products of the at least one target-sequence-specific FEN probe. The 5'-cleavage product of the at least one target-sequence-specific FEN probe is obtained only if the FEN probe hybridizes, by means of the target-sequence-specific 3' sequence thereof, to a complementary sequence segment of the at least one target sequence. The detection of the obtained plurality of template amplification products occurs distinctly and preferably by means of immunochromatographic methods.

Figure 3A:
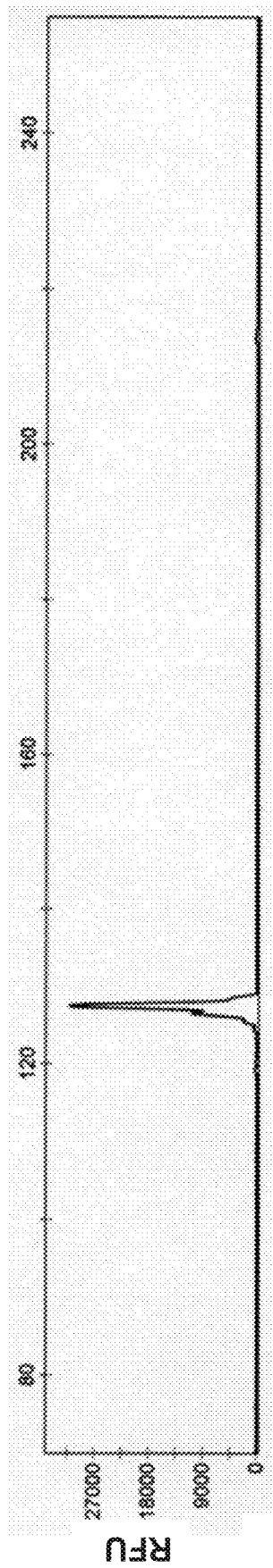

18 Claims, 5 Drawing Sheets
Specification includes a Sequence Listing.

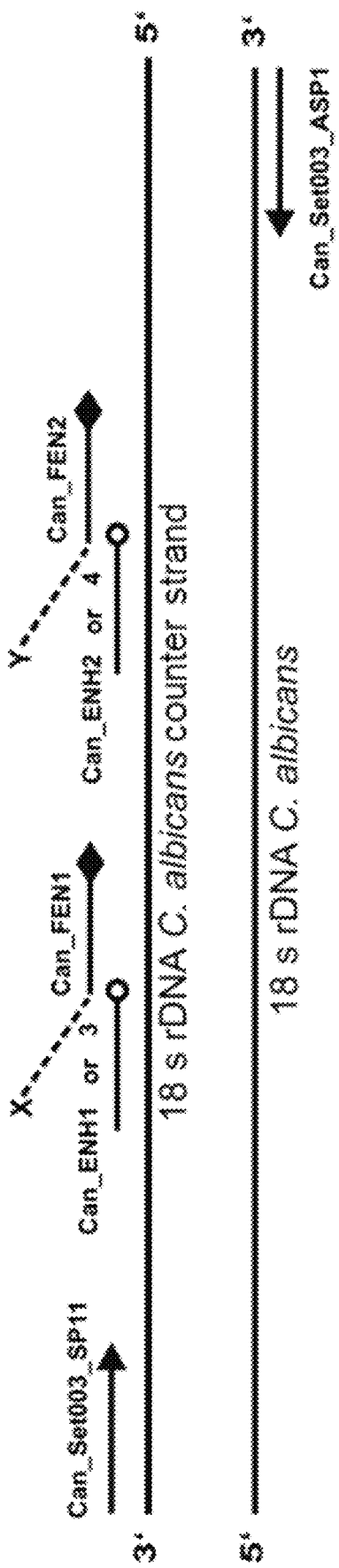
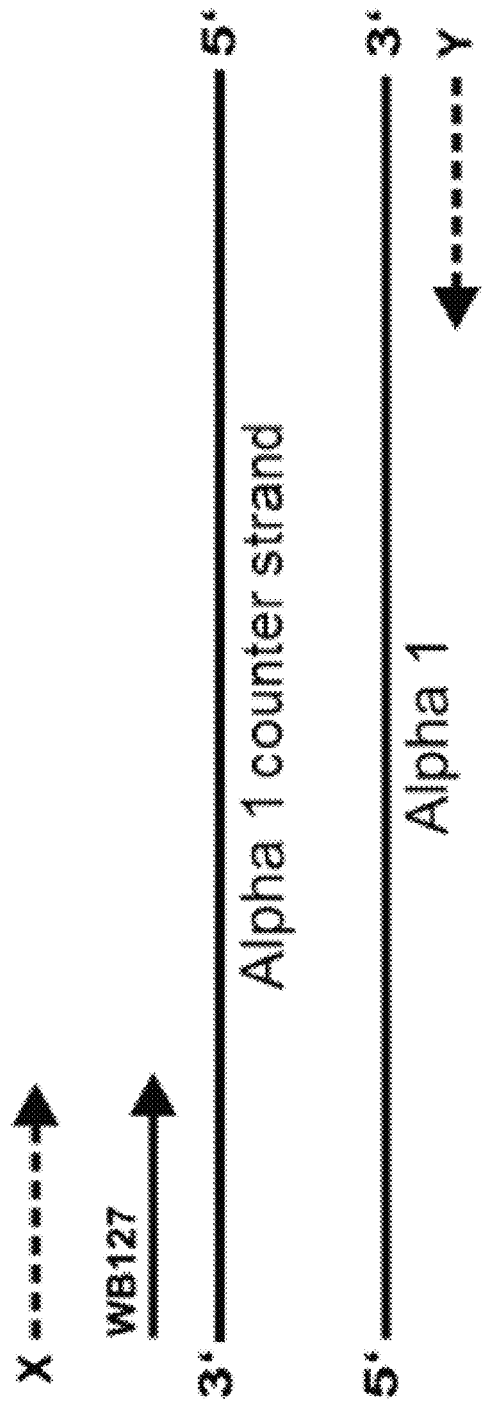
FIG. 1A
FIG. 1B

Can_FEN1  5'-X-TTAACTAGTACAATGAGTACAATGTAAATACCTTAACGAGGAACAAGATTGGAGGGCAAGTCTGGTGCCAGC-Spacer3-3'

Can_ENH1  5'-TTGGAATGAGTACAATGTAAATACCTTAACGAGGAACAAG-3'
Can_ENH3  5'-TTGGAATGAGTACAATGTAAATACCTTAACGAGGAACAAG-3'   -5'
target sequence  3'-AACCTTACTCATGTTACATTTATGGAATTGCTCCTTGTTAACCTCCGTTCAGACCACGGTCG-5'

FIG. 2A

Can_FEN2  5'-Y-CAACAGTTGCGCCAGCCTGAATGCGTACTGGACCCAGCC-Spacer3-3'

Can_ENH2  5'-CTTGGCTGGCCGGTCCATCTTTTTGAG-3'
Can_ENH4  5'-CTTGGCTGGCCGGTCCATCTTTTTGG-3'
target sequence  3'-GAACCGACCGGCCAGGTAGAAAACTACGCATGACCTGGGTCGGCTCGG-5'

FIG. 2B

SEQUENCE LISTING

```
<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: Artificially synthesized Can_Set003_SP11
      oligonucleotide primer

<400> SEQUENCE: 1
ggtaggatag tggcctacca tggttt                                        26

<210> SEQ ID NO 2
<211> LENGTH: 27
<212> TYPE: DNA
<213> ORGANISM: Artificial Sequence
<220> FEATURE:
<223> OTHER INFORMATION: Artificially synthesized Can_Set002_ASP1
``` oligonucleotide primer

<400> SEQUENCE: 2
ccgaccgtcc ctattaatca ttacgat                                           27

<210> SEQ ID NO 3
<211> LENGTH: 48
<212> TYPE: DNA
<213> ORGANISM: Artificial Sequence
<220> FEATURE:
<223> OTHER INFORMATION: Artificially synthesized Can_FEN1 FEN probe
<220> FEATURE:
<221> NAME/KEY: misc_feature
<222> LOCATION: (1)..(1)
<223> OTHER INFORMATION: /function = "X = absent or Hapten 2"
<220> FEATURE:
<221> NAME/KEY: misc_feature
<222> LOCATION: (48)..(48)
<223> OTHER INFORMATION: /function = "Spacer 3"

<400> SEQUENCE: 3
ttaactatgc ggcatcagag cagattggag ggcaagtctg gtgccagc                    48

<210> SEQ ID NO 4
<211> LENGTH: 43
<212> TYPE: DNA
<213> ORGANISM: Artificial Sequence
<220> FEATURE:
<223> OTHER INFORMATION: Artificially synthesized Can_FEN2 FEN probe
<220> FEATURE:
<221> NAME/KEY: misc_feature
<222> LOCATION: (1)..(1)
<223> OTHER INFORMATION: /function = "Y = 6FAM or Hapten 1"
<220> FEATURE:
<221> NAME/KEY: misc_feature
<222> LOCATION: (43)..(43)
<223> OTHER INFORMATION: /function = "Spacer 3"

<400> SEQUENCE: 4
caacagttgc gcagcctgaa tgcgtactgg acccagccga gcc                         43

<210> SEQ ID NO 5
<211> LENGTH: 24
<212> TYPE: DNA
<213> ORGANISM: Artificial Sequence
<220> FEATURE:
<223> OTHER INFORMATION: Artificially synthesized WB127F
      oligonucleotide primer

<400> SEQUENCE: 5
ttaactatgc ggcatcagag caga                                              24

<210> SEQ ID NO 6
<211> LENGTH: 24
<212> TYPE: DNA
<213> ORGANISM: Artificial Sequence
<220> FEATURE:
<223> OTHER INFORMATION: Artificially synthesized WB127FD
      oligonucleotide primer
<220> FEATURE:
<221> NAME/KEY: misc_feature
<222> LOCATION: (1)..(1)
<223> OTHER INFORMATION: /note = "Hapten 2"

<400> SEQUENCE: 6
ttaactatgc ggcatcagag caga                                              24

<210> SEQ ID NO 7
<211> LENGTH: 19

```
<212> TYPE: DNA
<213> ORGANISM: Artificial Sequence
<220> FEATURE:
<223> OTHER INFORMATION: Artificially synthesized Can_F1
      oligonucleotide primer

<400> SEQUENCE: 7
aaccttgggc ttggctggc                                              19

<210> SEQ ID NO 8
<211> LENGTH: 27
<212> TYPE: DNA
<213> ORGANISM: Artificial Sequence
<220> FEATURE:
<223> OTHER INFORMATION: Artificially synthesized Can_ENH2
      oligonucleotide primer

<400> SEQUENCE: 8
cttggctggc cggtccatct ttttgag                                     27

<210> SEQ ID NO 9
<211> LENGTH: 40
<212> TYPE: DNA
<213> ORGANISM: Artificial Sequence
<220> FEATURE:
<223> OTHER INFORMATION: Artificially synthesized Can_ENH1
      oligonucleotide primer

<400> SEQUENCE: 9
ttggaatgag tacaatgtaa ataccttaac gaggaacaag                       40

<210> SEQ ID NO 10
<211> LENGTH: 39
<212> TYPE: DNA
<213> ORGANISM: Artificial Sequence
<220> FEATURE:
<223> OTHER INFORMATION: Artificially synthesized Can_ENH3
      oligonucleotide primer

<400> SEQUENCE: 10
ttggaatgag tacaatgtaa ataccttaac gaggaacag                        39

<210> SEQ ID NO 11
<211> LENGTH: 26
<212> TYPE: DNA
<213> ORGANISM: Artificial Sequence
<220> FEATURE:
<223> OTHER INFORMATION: Artificially synthesized Can_ENH4
      oligonucleotide primer

<400> SEQUENCE: 11
cttggctggc cggtccatct ttttgg                                      26

<210> SEQ ID NO 12
<211> LENGTH: 127
<212> TYPE: DNA
<213> ORGANISM: Candida albicans

<400> SEQUENCE: 12
ttaactatgc ggcatcagag cagattgtac tgagagtgca ccatatgcgg tgtgaaatac   60
cgcacagatg cgtaaggaga aaataccgca tcaggcgcca ttcgccattc aggctgcgca  120
actgttg                                                           127
```

CONFIRMATION TEST FOR PRIMARY NUCLEIC ACID AMPLIFICATION PRODUCTS IN A CONTINUOUS REACTION SETUP AND IMMEDIATE ANALYSIS VIA IMMUNOCHROMATOGRAPHIC METHODS

The present invention relates to a method for confirmation of amplified nucleic acid target sequences (target sequence), preferably from human samples, during an amplification reaction in a collective and continuous reaction setup as single-tube process, wherein confirmation of the target sequence amplification product is obtained via a hapten pair-labelled artificial matrix amplification product. The artificial matrix sequence is thereby amplified and optionally labelled via the 5'-cleavage product of the at least one target sequence-specific FEN probe. The 5'-cleavage product of the at least one target sequence-specific FEN probe is obtained only if the FEN probe with its target sequence-specific 3'-sequence hybridizes to a complementary sequence fragment of the at least one target sequence. Detection of the plurality of matrix amplification products obtained is carried out distinctly and preferably via immunochromatographic methods.

Nucleic acid amplification technologies (NAT), most notably the polymerase chain reaction (PCR), are nowadays an essential component of molecular genetic diagnostics. In this context, various parameters are also verifiable in so-called multiplex methods.

In order to increase the specificity and, in particular, for quality assurance of the molecular nucleic acid verification of pathogens, a confirmation test for amplification products is required (MIQ-1 2011, Rili-BÄK-B3 2013). For this purpose, DNA probes are often used, for example in homogenous test methods (so-called single-tube processes or reactions, such as e.g. the real time PCR), which sequence-specifically hybridize with a DNA half strand of the DNA amplification product and are labeled with a fluorophore pair interacting via FRET (Förster resonance energy transfer). The FRET is modulated or ceased by the sequence-specific hybridizing with the result that a signal measurable via real time thermal cyclers occurs. So-called hydrolysis probes cleaved by the intrinsic nuclease activity of the Taq DNA polymerase after hybridization, whereby the fluorophore pair is separated, are a preferred probe format.

As an alternative to homogenous tests, method steps downstream of the NAT, such as hybridization of the DNA amplification products to immobilized probes (e.g. reverse line blot, lateral flow immunochromatographic test, DNA chip, DNA bead assay), Southern hybridization, DNA sequencing or nested PCR, may be performed as a confirmation test. However, these strategies require additional processing steps for the confirmation test which are more time and cost intensive and involve the risk of contamination.

Contamination of the amplification products occurs upon removing an aliquot from the PCR reaction setup and/or upon conveying this aliquot in a new reaction setup for the downstream method for confirmation of the amplification products. In particular, contamination comprises pollution of the amplification product with foreign DNA or amplification products of samples processed in parallel (cross-contamination).

Contamination has a huge impact on the quality of the confirmation test. Considering the highly sensitive scope of application of such confirmation tests, such as diagnostics, tumor diagnostics, diagnostics of serious infectious agents and their resistances, a confirmation test decides on diagnosis and therapy of a patient resulting thereof. Misdiagnoses results in wrong therapies, consequential damages to the patient and increased costs for the health care system.

Therefore, a reliable confirmation test is essential. It should be simple and robust so that error rates are as reduced as possible.

Confirmation of NAT amplification products via fluorescent dyes which sequence-unspecifically bind double-stranded DNA (e.g. SYBR Green I), or, solely, via size determination of the primary amplification products by downstream DNA electrophoreses (slab gel or capillary gel electrophoresis) are not recognized methods according to the mentioned guidelines.

The relatively low multiplex capability of real time thermal cyclers which currently have only 3-6 different detection channels is a disadvantage of homogenous test methods.

Moreover, there is a great need for molecular genetic test formats to tap into point of care or point of need diagnostics. This in particular applies to containment of pathogens and verification of their antibiotic resistances in resource-pour environments. Lateral flow immunochromatographic tests (LFT) have already proven their worth in these fields of application for verification of antigens and other binding ligands (Hu et al. 2014).

In particular, LFT are well-established for the verification of analytes from the substance groups of proteins, carbohydrates as well as certain drugs and toxins. However, there are still multiple technical limitations existing for the practicability of LFT being intended for the verification of nucleic acid amplification products (nucleic acid lateral flow test, NALFT). In particular, this relates, as stated below, also to a confirmation test for nucleic acid amplification products.

DE10154291B4 describes e.g. a quick test, in which DNA hybridizing with immobilized target sequence-specific oligonucleotide probes is carried out in the detection region of an LFT stripe after a PCR or multiplex PCR. In addition, EP1623042B1 discloses a DNA hybridization with single-stranded probes being present in the conjugate zone of an LFT stripe. Both methods require denaturing running buffers and sequence-specific adjustments of the hybridization conditions, which, in particular, make test development difficult and presume controlled ambient temperatures for the performance of the LFT.

In order to avoid the afore-mentioned adjustments, hybridization probes may be carried along in the PCR setup. However, a disadvantage of this strategy is that hybridization of the probe is in competition with primer elongation by the DNA polymerase or rehybridization of the DNA half strands of the nucleic acid amplification products, respectively, being present in high concentration at the end of NAT. Additional signal losses must be considered using the widely used Taq DNA polymerase due to the intrinsic nuclease activity of the enzyme. Due to these dependencies, there is a loss in quality of the method. As a result, attempts have been made within the frame of the experiments of the present invention to find a solution approach avoiding the aforementioned disadvantages to overcome the limitation of the aforementioned tests from the state of the art.

In contrast, hapten-based LFT stripes may be used with a universal running buffer at variable ambient temperatures. They are functionalized with hapten-specific receptor molecules (e.g. antibodies, streptavidin) in the detection zone. For example, colloidal gold being conjugated with two independent hapten-specific receptor molecules is introduced in the conjugate reservoir of the LFT stripe for visual or device-based optical verification. Methods for labelling of oligonucleotides with different haptens (e.g. biotin, digoxigenin, o-nitrophenol, peptides, fluorophores) are described. DNA amplification product verification succeeds by only one DNA half strand is labelled during PCR via a primer which e.g. carries the hapten of the colloidal gold conjugate. Subsequently, an aliquot of the PCR amplification product is diluted in running buffer and incubated in the presence of a target sequence-specific oligonucleotide probe which hybridizes with the DNA half strand already being single-labelled and is labelled with a hapten binding to a receptor molecule of the detection zone. However, this additional hybridization step downstream of the PCR shows the above mentioned disadvantages and should therefore be avoided.

Therefore, it was an aim of the present invention to tap into and/or to simplify the provision of confirmation tests for diagnostic tests being tied to the performance of appropriate confirmation tests. A simplified confirmation test (synonymous confirmation assay) for NAT for a NALFT for point of care or point of need diagnostics is presented.

The object of the present invention is to provide a continuous and collective reaction setup for the amplification of target sequences, in particular from human samples, such as blood, plasma, bone and/or tissue, and at the same time for the subsequent confirmation test. It is also an aim to provide a method, in particular a single-tube process, for amplification and confirmation of the respective target sequence using the aforementioned reaction setup. In this context, intermediate steps for further processing of the amplification products obtained, such as purification and/or additional probe hybridizations, in separated vessels should be avoided. Thus, it is a further aim of the present invention to avoid the risk of contamination with foreign DNA, RNA, proteins, peptides and/or chemicals and further to provide a simplified and faster method. A method avoiding the disadvantages and risks from the state of the art and at the same time combines the advantages and potentials of existing multiplex verification methods should be provided. Therefore, a further object is the provision of a method for amplification of at least one target sequence, in particular from a human sample of a patient, and a continuously following confirmation of the at least one target sequence and detection via an immunochromatographic method, such as the nucleic acid lateral flow (NALFT) method. Thus, a further aim of the present invention is the provision of a method which may be supplied with a continuous reaction setup and the amplification products obtained therefrom to variable detection methods having a solid phase without processing steps. A test for diagnostics, in particular human diagnostics, having a low error rate in confirmation of the respective amplification product should be provided such that the risk of contamination is reduced to prevented. A confirmation assay with high sensitivity for samples having low quality and/or very low usable DNA amounts should also be provided. The reaction setup, the multiplex kit and the confirmation assay should easily and location-independently (point of need) be used and performed at the same high quality. An essential aim is to provide a confirmation test meeting the requirements of at least the guideline MIQ-1 2011 for nucleic acid amplification techniques and/or the guideline of the German Medical Association B3 (Rili BÄK-B3) for direct verification and characterization of infectious agents, as well as respectively meeting the requirements of the respective amendments of the guideline.

Therefore, the present invention provides a method being characterized by the confirmation test (synonymous=confirmation assay) according to the invention in which a homogenous PCR or multiplex PCR without additional pipetting steps (single-tube process) is performed.

The essential advantages of the present invention are that a single-tube process for confirmation of target sequences is provided, and the homogenous test format according to the invention provides the possibility to quantify the starting nucleic acids, as described below. In this way, a further advantage of the present invention is that samples having only very low amount of usable DNA starting material and/or degraded DNA starting material may nevertheless be used as target sequence and confirmed and detected according to the invention. In Example 3, FIG. 5, a successful verification of very low DNA amounts is shown for selected combinations (Table 3) of the components of the reaction setup according to the invention.

The probes preferably used are so-called hydrolysis probes which are directly contained in the PCR reaction setup and are cleaved by the intrinsic nuclease activity of the Taq DNA polymerase after hybridization to the target sequence. In this way, e.g. in HIV diagnostics, the virus load of the patient as well as the therapeutic success after medication may be determined. The confirmation assay according to the invention has the particular advantage that FEN probes according to the invention, possibly still being present in excess at the end of the amplification reaction, in particular PCR, are not reactive. This means that the excess FEN probes do not interfere the confirmation and detection of the matrix amplification products obtained.

Thus, the confirmation assay according to the invention has the advantage of being more sensitive due to exponential signal enhancement and allowing a higher multiplex degree.

In addition, the confirmation test may be conceptualized independently from the target nucleic acid to be amplified as standardized universal reaction steps. The latter allows preparation of a test-independent development tool consisting of universal PCRs and/or universal primer elongation reactions.

The reaction products (synonymous=amplification products, matrix amplification products) of the confirmation test are compatible with standard method steps for verification via lateral flow immunochromatography.

The solution according to the invention will be described in the following. Selected embodiment examples show ways for achievement of the solution according to the invention and explain the basic principle and operation principle of the present invention, wherein the examples presented herein are not to be construed restrictively.

A first subject matter of the present invention is a confirmation, in particular a confirmation assay, of at least one amplified nucleic acid target sequence, in particular DNA and/or cDNA, which is subsequently shortly referred to as target sequence, during a amplification reaction in a collective and continuous reaction setup containing a reaction mixture comprising at least one target sequence to be verified, at least two target sequence-specific primers (P1, P2, $P_{1-n}$) being suitable for amplification of the at least one target sequence, at least one labelled target sequence-specific, in particular intermolecular, flap endonuclease probe (FEN probe FEN1, $FEN_{1-n}$), wherein the at least one, in particular single-stranded, FEN probe comprises a target sequence-specific 3'-sequence, in particular DNA 3'-sequence, which is complementary to a sequence fragment of the at least one target sequence within a region being restricted on the target sequence by the at least first primer (P1) and the at least second primer (P2), in particular P1 and P2 hybridize with the target sequence (see FIG. 1)

a protective group at the 3'-end of the target sequence-specific 3'-sequence, in particular as polymerase blocker, preferably the 3'-OH group is missing or it is covalently modified, and a target sequence-unspecific 5'-sequence, in particular DNA 5'-sequence, which is labelled at its 5'-end with one hapten of a specific hapten pair, in particular with a detector hapten or a hapten being sequence-specific to the matrix sequence, and at least one artificial matrix sequence, in particular artificial nucleic acid sequence, the confirmation assay comprises per cycle of the amplification reaction the steps of hybridization of the target sequence-specific 3'-sequence of the at least one labelled FEN probe to a complementary sequence of the at least one target sequence to be verified, cleavage of the at least one labelled FEN probe ($FEN_{1-n}$), in particular obtaining of at least one free 5'-cleavage product ($S_{1-n}$), being labelled with one hapten of a specific hapten pair at the 5'-end, each comprising the target sequence-unspecific 5'-sequence hybridization of the at least one labelled 5'-cleavage product ($S_{1-n}$) of the at least one FEN probe ($FEN_{1-n}$) to a complementary sequence of the at least one artificial matrix sequence, in particular to the matrix sequence of a denatured double strand, in particular of a single strand, in particular elongation of the at least one labelled 5'-cleavage product ($S_{1-n}$) being hybridized to the preferably single-stranded artificial matrix sequence, amplification of the at least one artificial matrix sequence using the at least one labelled 5'-cleavage product ($S_{1-n}$) of the at least one FEN probe, and labelling of the at least one artificial matrix sequence during amplification by the at least one 5'-cleavage product ($S_{1-n}$) of the at least one FEN probe (FEN1, $FEN_{1-n}$), preferably by the one hapten of a specific hapten pair from the 5'-end of the 5'-cleavage product (S1, $S_{1-n}$) and by a second hapten of a 5'-cleavage product (S2, $S_{1-n}$) of a second FEN probe (FEN2, $FEN_{1-n}$) or of a further primer (M1), and in particular obtaining of at least one, preferably labelled artificial matrix sequence amplification product (synonymous=artificial matrix amplification product, matrix amplification product), and in particular detection of the at least one optionally labelled matrix sequence amplification product, preferably the optionally labelled matrix sequence amplification product is detected in a liquid phase, particularly preferably via an immunochromatographic method.

The method described afore with the continuous and collective reaction setup for amplification of the target sequence and confirmation of the target sequence amplification products obtained via amplification and labelling of a matrix sequence may synonymously referred to as single-tube process since the aforementioned reactions are carried out without processing steps and without temporal or spatial separation. The person skilled in the art knows that any further components, such as e.g. buffer systems, nucleotides, salts etc., being required for a successful PCR, are also contained in the reaction mixture. After obtaining of the, optionally labelled, matrix sequence amplification product, detection may be performed with the desired method and device at any time and location-independently.

A target sequence is a nucleic acid sequence within a sample (synonymous=specimen) serving for e.g. specific verification of an individual (forensics, genealogy), of a species (e.g. pathogen, genetically modified organisms), of a disease or of another biological characteristic within the frame of an analytics or diagnostics. The sample comprises any conceivable source materials having biological amount such as e.g. vegetable, animal and human liquids, extracellular circulatory liquids, in particular blood, plasma, serum and/or lymph, digestive juices, in particular saliva, gastric juice, juice of the pancreas and/or gall, secretions and excretions, in particular sweat, urine, faeces, ejaculate, vaginal secretions, tear fluids, nasal secretion and/or mother's milk and/or further liquids or secretions, in particular amniotic fluid, cerumen, cerebral fluid and/or pus and tissue, nails, hairs and/or bone constituents, foodstuffs, environmental isolates etc., and/or synthetic nucleic acids (e.g. barcode sequences and other targeted DNA-labelling of other articles), and may comprise one or more target sequences. Sample comprises biopsy material and smear material also. Preferably the sample is a human sample.

The target sequence in the aforementioned assay preferably is a DNA, in particular natural DNA and/or cDNA (English complementary DNA, German komplementäre DNS) having been synthesized via a reverse transcriptase from RNA, such as mRNA or ncRNA. In particular in medical diagnostics, ribonucleic acids usable from samples are transcribed into cDNA to subsequently supply them as target sequence to analytics, in particular to the assay according to the invention. In particular, the target sequence to be verified according to the invention is a target sequence which is present in multiple copies per cell, comprising mitochondrial DNA (mtDNA), rDNA, SINE (short interspersed nuclear element, Alu family) and/or MIR (mammalian-wide interspersed repeats). Preferably, it is a double-stranded DNA.

According to the invention, the target sequence is thereby duplicated (synonymously amplified) in a amplification reaction, preferably in a amplification reaction of a polymerase chain reaction (PCR) or an isothermal nucleic acid amplification technology (iNAT). PCR is known by the person skilled in the art. Nucleic acid amplification technologies (NAT) refer to enzymatic methods for in-vitro amplification of nucleic acids, in particular of target sequences according to the invention. They may require thermic cycles (e.g. PCR) or proceed isothermally (iNAT), The assay according to the invention may be used for confirmation of both variants. Further embodiments of the aforementioned methods iNAT are LAMP (loop-mediated isothermal amplification), HDA (helicase-dependent amplification), RPA (recombinase polymerase amplification), SIBA (Strand Invasion Based Amplification), RCA (rolling circle amplification).

According to the invention, flap endonuclease probes, shortly referred to as FEN probes, are molecules comprising a, in particular single-stranded, nucleic acid sequence, which has at least two functional regions. The two functional regions are a 5'-sequence not being complementary to a sequence fragment of the at least one target sequence (shortly referred to as target sequence-unspecific 5'-sequence) and a 3'-sequence being complementary to a sequence fragment of the at least one target sequence (shortly referred to as target sequence-specific 3'-sequence). The sequence fragment is located within a region being restricted on the target sequence by the at least first primer (P1) and by the at least second primer (P2). The FEN probes hybridize with the target sequence forming a 5'-flap cleavable by a FEN, which is represented by the target sequence-unspecific 5'-sequence. The term flap refers to fork-shaped unpaired structures within or at the end (3' or 5') of a DNA double helix. The flap endonuclease (FEN) recognizes these structures as substrate, as shown in FIG. 1 and FIG. 2. According to the invention, the 3'-OH end of the FEN probe is protected by a so-called polymerase blocker against elongation by a DNA polymerase. The FEN probe is cleaved based on the influence of a FEN (flap endonuclease), wherein a free 5'-cleavage product ($S_{1-n}$) is obtained.

FEN1 shortly stands for one FEN probe and FEN1 and FEN2 shortly stand for two FEN probes. Correspondingly, S1 stand for one 5-cleavage product and S1 and S2 stand for two 5-cleavage products. The term FEN stands for at least one to variably many FEN probes or $S_{1-n}$ stands for relatively many 5'-cleavage products of the respective FEN probe, wherein n is equal to an integer. In particular, n is an integer and preferably equal to 2, 3, 4, 5, 6, 7, 8, 9 or 10 (FEN1-10 correspond to ten, in particular different, FEN probes) etc, to less than or equal to 50 FEN probes. The highest possible number of FEN probes in a reaction mixture according to the inventions depends on the method used for detection. The number of the detection channels in the device used and the maximum distinct resolution of different, in particular artificial and optionally labelled, matrix amplification products limit the maximum usable number of the FEN probes according to the invention.

Figure 4:
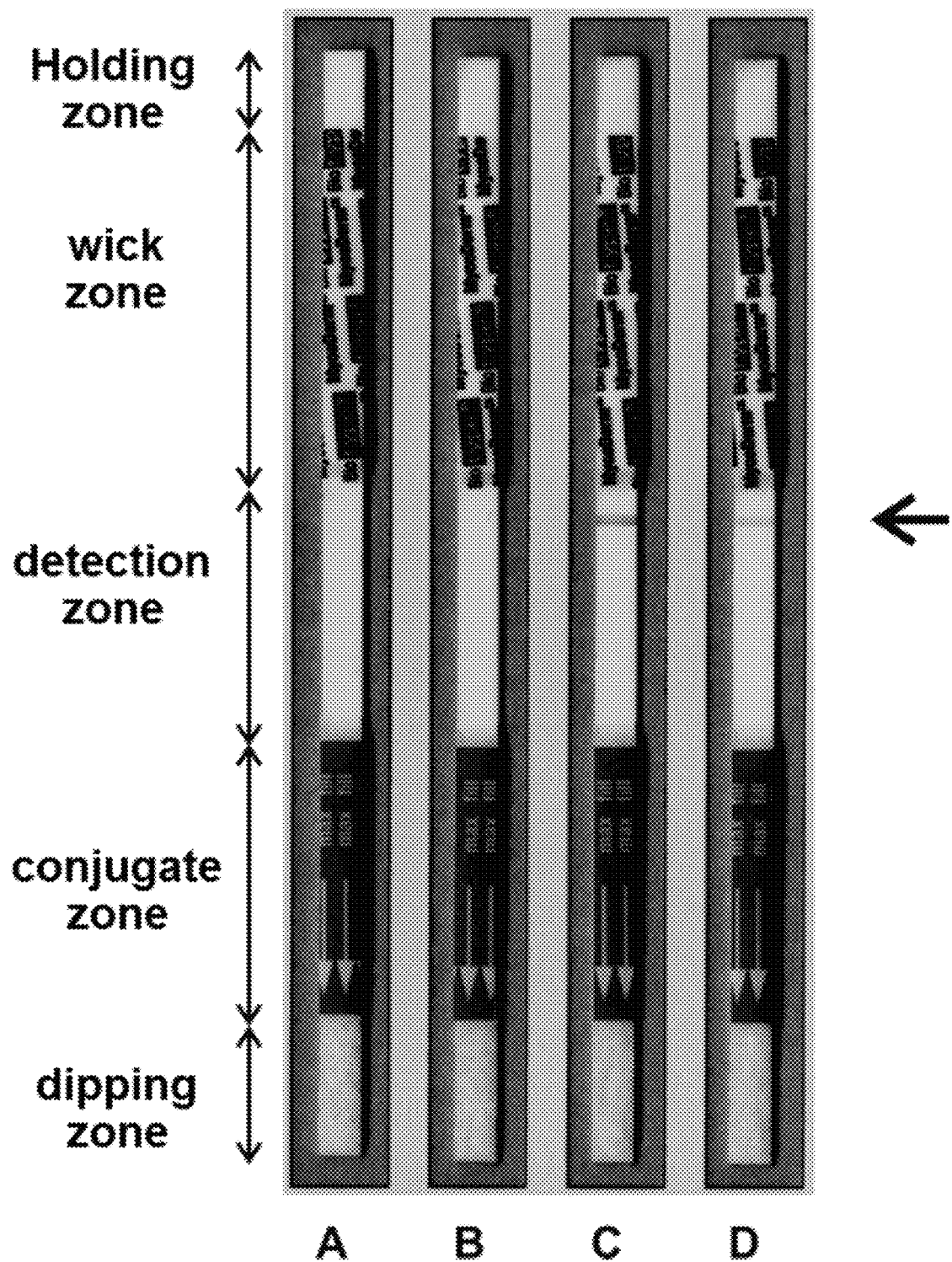

Relating to the detection method based on a solid phase for separation of the matrix amplification products, in particular lateral flow methods as shown in FIG. 4, the design of the solid phase, in particular of the detection zone, influences the maximum usable number of labelled FEN probes according to the invention and/or of further primers (M1) as well as of the artificial matrix sequences and thus the maximum possible number of distinctly verifiable matrix amplification products.

The protective group has the function of a polymerase blocker, wherein the protective group protects the 3'-end of an oligonucleotide against an elongation by a DNA polymerase. In this case, a recognition reaction between the 3'-end of the 3'-sequence of the at least one labelled FEN probe and a polymerase is blocked so that the 3'-end do not function as primer. According to the invention, this may be attained by the absence of the 3'-OH group (3'-dideoxynucleotide), by chemical modification of the 3'-OH group comprising 3'-phosphate, 3'-spacer C3 (3'-hydroxypropyl-phosphate), amino, A-alkyl, 3'-inverted nucleotide, i.a. and/or by additional nucleotides not pairing with the target sequence.

Flap endonucleases (FEN) are structure- and strand-specific endonucleases which cleave the single-stranded DNA- or RNA-sequence of a fork-shaped unpaired 5'-end (5'-flap) of a DNA double helix (Lyamichev et al. 1993). FEN occur in all living organisms and release in conjunction with further enzymes, in particular during DNA replication, the so-called Okazaki fragments (RNA-DNA hybrids) at the remaining strand of the replication fork (DNA repair function), Eubacterial FEN form in combination with a DNA polymerase of type Pol 1 (synonymous=Pol A) a protein unit (e.g. Pol 1 of *Escherichia coli, Thermus aquaticus, T. thermophilus, Aquifex* spp.). Archaebacterial (e.g. *Archaeoglobus fulgidus, Pyrococcus* spp., *Methanocaldococcus jannaschii, Methanothermobacter thermoautotrophicum*) and eukaryotic FEN (e.g. *Homo sapiens*) represent autonomous proteins.

The artificial matrix sequence (synonymously also referred to as matrix sequence or matrix) contained in the reaction mixture is a nucleic acid sequence which is bioinformatically designed with the minimum demand that it does not match any specific primer binding sites and probe binding sites of the target sequence being used in the multiplex. Thus, the artificial matrix sequence has no sequences being complementary to the specific primer binding sites and probe binding sites of the target sequence. In particular, it must not function as a DNA matrix for any target sequence-specific primer of the multiplex. The ends of the artificial matrix sequence or of its counter strand carry binding sites for different 5'-cleavage products of at least one labelled FEN probe, preferably of two differently labelled FEN probes, or for at least one labelled 5'-cleavage product of a FEN probe as well as of an additional artificial primer M1. The 5'-cleavage product of a FEN probe, labelled at the 5'-end, has a free 3'-OH end and has the function of a primer which is complementary to the 5'→3'-sequence of an artificial matrix sequence or to the counter strand of the artificial matrix sequence and is an essential component of the confirmation test according to the invention.

A further primer M1 (in the examples referred to as WB127) refer to a primer which does not show any cross hybridizations with all of the target sequences of the multiplex and forms a DNA double helix elongatable by DNA polymerase with the counter strand of at least one artificial matrix sequence.

Multiplex describes amplification and confirmation of multiple target sequences in one reaction setup. The genetic fingerprint of human by genotyping of 20 and more short tandem repeats, differential diagnostics of different somatic mutations in tumors, clarification of organ-specific infections (e.g. lung, intestine, sexually transmitted infections) by verification of specific pathogen groups and/or amplification of nucleic acid libraries (panels) are examples for multiplex methods. Preferably, the method according to the invention is a multiplex method which may be used for any desired type—equal or analogous to the stated examples—of verification.

In an embodiment of the confirmation assay according to the invention, the protective group comprises at the 3'-end of the 3'-sequence of the at least one, in particular single-stranded, FEN probe instead of a 3'-OH group a nucleic acid sequence, in particular a DNA sequence greater than or equal to 1 base to less than or equal to 5 bases, which is not complementary to the target sequence. Preferably, the sequence comprises 1, 2, 3, 4, or 5 bases. 1 or 2 bases are particularly preferred.

In a further embodiment of the confirmation assay according to the invention, the reaction mixture further comprises at least one enzyme being suitable for cleavage of the at least one FEN probe, which is selected from a FEN as intrinsic component of a DNA polymerase or as enzyme separated from a polymerase.

Preferably, the reaction mixture according to the invention comprises at least one polymerase having intrinsic endonuclease activity which is selected from eubacterial FEN forming in combination with a DNA polymerase of type Pol 1 (synonymous=Pol A) a protein unit. As a result, this polymerase has its imminent, thus intrinsic, FEN activity. Such FEN are to be found in species e.g. *Escherichia coli, Thermus aquaticus, T. thermophilus* and/or *Aquifex* spp, whose polymerases may respectively be used according to the invention. Within the sense of the invention, a Taq DNA polymerase from *Thermus aquaticus* having intrinsic FEN activity is particularly preferably used.

Alternatively, according to the invention, the reaction mixture may comprise a polymerase and a separated FEN, wherein the FEN is preferably selected from archaebacterial FEN and/or eukaryotic FEN. In the following species *Archaeoglobus fulgidus, Pyrococcus* spp., *Methanocaldococcus jannaschii, Methanothermobacter thermoautotrophicum* and/or *Homo sapiens* the FEN is an autonomous protein, which may be used according to the invention. Preferably in combination with a polymerase. Particularly preferably, thermostable DNA polymerases and thermostable FEN are used.

In a further embodiment, it is conceivable that a polymerase having intrinsic FEN activity is used and a separated FEN is additionally added. This is advantageous if the polymerase has excellent activity but its FEN activity is not reliable, too low and/or has other unfavorable biochemical characteristics (e.g. flap substrate specificity, pH, salt ion and temperature optimum). In this case, a combination of the at least one suitable polymerase, having or lacking intrinsic FEN activity, with at least one or more FEN is preferable. The combination of the aforementioned enzymes depends on the sample to be analyzed and/or the further components of the reaction mixture according to the invention, and is to be adjusted on a case-by-case basis.

In a further embodiment of the confirmation assay according to the invention, the aforementioned reaction mixture additionally comprises at least one FEN enhancer oligonucleotide (e.g. Can_ENH1, Can_ENH2, Can_ENH3 and/or Can_ENH4), in particular for increase of the intrinsic FEN activity of a polymerase, preferably of the Taq DNA polymerase. Preferably, the addition of FEN enhancer oligonucleotides ($ENH_{1-n}$) increases the intrinsic FEN activity of a polymerase, preferably of the Taq DNA polymerase, at least quantitatively and optionally qualitatively. The at least one FEN enhancer oligonucleotide ($ENH_{1-n}$) overlaps with its sequence at the 3'-end by at least one base with the target sequence-specific 3'-sequence at the 5'-binding site of the at least one FEN probe, as shown in FIG. 1. In $ENH_{1-n}$ n is an integer. Preferably greater than or equal to 1 to less than or equal to 50. In particular, n is an integer and preferably equal to 2, 3, 4, 5, 6, 7, 8, 9 or 10. Can_ENH1, Can_ENH2, Can_ENH3 and/or Can_ENH4 are examples for FEN enhancer nucleotides according to the invention.

A further subject matter of the present invention is the aforementioned reaction mixture, in particular for use in the confirmation assay according to the invention, comprising
   at least two target sequence-specific primers (P1, P2, $P_{1-n}$) being suitable for amplification of at least one target sequence to be verified,
   at least one labelled target sequence-specific, in particular intermolecular, flap endonuclease probe according to the invention (FEN probe FEN1, $FEN_{1-n}$), and
   at least one artificial matrix sequence, in particular artificial nucleic acid sequence,
   optionally, at least one further primer (M1) binding to the complementary strand of the at least one artificial matrix sequence, and/or
   optionally, at leas one FEN enhancer oligonucleotide ($ENH_{1-n}$).

Thus, an embodiment of the reaction mixture according to the invention, in particular for verification of a target sequence in the frame of in-vitro diagnostics, comprises
   additionally at least one target sequence to be verified, in particular within a biological sample, preferably human sample
   at least two target sequence-specific primers according to the invention (P1, P2, $P_{1-n}$),
   at least one target sequence-specific labelled FEN probe according to the invention (synonymous=FEN probe) (see FIG. 1),
   at least one artificial matrix sequence, in particular artificial nucleic acid sequence,
   at least one FEN enhancer nucleotide (e.g. Can_ENH1, Can_ENH2, Can_ENH3 and/or Can_ENH4).

In a further preferred embodiment of the confirmation assay according to the invention, the content of the at least one target sequence to be verified, preferably DNA, is greater than or equal to 2 copies in the reaction mixture according to the invention, in particular in a reaction mixture containing at least one FEN enhancer nucleotide ($ENH_{1-n}$). Preferably, the content of the at least one target sequence to be verified is greater than or equal to 5, greater than or equal to 10, greater than or equal to 15, greater than or equal to 20, greater than or equal to 25, greater than or equal to 50, greater than or equal to 100 copies and, particularly preferably, to respectively less than or equal to 1000 copies, respectively as final concentration based on the total reaction mixture.

In a further preferred embodiment of the confirmation assay according to the invention, the content of the at least one target sequence to be verified, preferably DNA, is greater than or equal to 10 copies in the reaction mixture according to the invention, in particular in a reaction mixture without FEN enhancer oligonucleotides ($ENH_{1-n}$). Preferably, the content of the at least one target sequence to be verified is greater than or equal to 15, greater than or equal to 20, greater than or equal to 25, greater than or equal to 35, greater than or equal to 50, greater than or equal to 75, greater than or equal to 100, greater than or equal to 150, greater than or equal to 250 copies and, particularly preferably, to respectively less than or equal to 1000 copies, respectively as final concentration based on the total reaction mixture.

The aforementioned lower limits were determined on the basis of the DNA amount [fg] of the *C. albicans* target sequence actually used, in examples 1-3, wherein 2 fg of a double-stranded DNA correspond to approximately 10 copies of a target sequence to be verified (conversion see Example 3).

In particular, the target sequence to be verified according to the invention, preferably DNA, particularly preferably a double-stranded DNA, is a target sequence which is present in multiple copies per cell, comprising mitochondrial DNA (mtDNA), rDNA, SINE (short interspersed nuclear element, Alu family) and/or MIR (mammalian-wide interspersed repeats).

In a further embodiment of the confirmation assay according to the invention, the at least one target sequence to be verified, in particular comprising RNA, DNA, cDNA and/or rDNA, preferably a target sequence which is present in multiple copies per genome, is present within a biological sample, in particular a human sample. Particularly preferably, the human sample comprises at least one target sequence to be verified
   of a liquid comprising extracellular circulatory liquids, such as blood, plasma, serum and/or lymph, digestive juices, such as saliva, gastric juice, juice of the pancreas and/or gall, secretions
   of an excretion, such as sweat, urine, feces, ejaculate, vaginal secretions, tear fluid, nasal secretion and/or mother's milk,
   of a further liquid or secretion, such as amniotic fluid, cerumen, cerebral fluid and/or pus, and/or
   of a tissue, nails, hairs and/or bone constituents.

Different combinations were tested according to the invention for verification of the influence of the FEN enhancer oligonucleotides ($ENH_{1-n}$) on the strength of the signal. The experiments and results described herein, as shown in Example 1 and Table 2, were analysed via an electrophoretic method due to limited resources. The results apply correspondingly for hapten pair-labelled matrix amplification products and the embodiments according to the invention required for use with immunochromatographic methods, preferably NALFT. A selected embodiment for NALFT is shown in Example 2, FIG. 4 as well as in Example 3, FIG. 5.

In a preferred embodiment, the reaction mixture according to the invention comprises at least one labelled FEN probe (FEN1) and at least one FEN enhancer oligonucleotide (e.g. Can_ENH1, Can_ENH2, Can_ENH3 and/or Can_ENH4). An example according to the invention in shown in Table 2. Surprisingly, already the combination of only one FEN probe, e.g. Can_FEN2, and only one FEN enhancer oligonucleotide, e.g. Can_ENH2, achieves a 5-fold stronger signal (4954 RFU) in the confirmation assay with an electrophoretic detection method in comparison with a confirmation assay with only one FEN probe or two differently labelled FEN probes, e.g. Can_FEN2 and Can_FEN1 (900/931 RFU). An appropriate signal increase is to be expected in the immunochromatographic method, preferably NALFT.

Thus, the addition of the at least one FEN enhancer oligonucleotide (e.g. Can_ENH1, Can_ENH2, Can_ENH3 and/or Can_ENH4) in the confirmation assay according to the invention surprisingly results in an at least 5-fold enhancement of the signal of the at least one matrix sequence amplification product obtained, preferably in the immunochromatographic method.

Selected combinations of FEN probes, FEN enhancer oligonucleotides and of the further primer M1 (see Table 3) from Example 1 were analyzed in more detail in Example 3 depending on the content of the target sequence to be verified (DNA source material in a biological sample). The reaction mixture comprising a FEN probe (FEN1) and a further primer (M1) as well as the reaction mixture comprising a FEN probe (FEN1), a further primer (M1) and a FEN enhancer oligonucleotide (ENH1), each providing excellent signals (5900 RUF or 4213 RFU, respectively) in capillary electrophoresis at 50 pg DNA source material in Example 1, already enabled visually evaluable verifications even at low DNA amounts of merely 20 fg or 2 fg, respectively, in the immunochromatographic method on the basis of distinct bands in the detection field of the LFT (Example 3, FIG. 5: reaction mixtures 3 or 11 and 18).

A FEN enhancer oligonucleotide ($ENH_{1-n}$) hybridizes with the target sequence immediately upstream of the target sequence-specific 3'-sequence of a FEN probe. In this case, the 3'-end of the FEN enhancer oligonucleotide ($ENH_{1-n}$) overlaps with the part of the FEN probe, which is paired with the target sequence exactly to the double helix, by at least one nucleotide. The 3'-sequence of the FEN enhancer oligonucleotide overlapping with the FEN probe does not necessarily have to thereby hybridize with the target sequence but may form an unpaired 3'-flap (Kaiser et al. 1999). This arrangement results in a significant increase in cleavage activity of the intrinsic FEN of a polymerase, preferable of the Taq DNA polymerase. Other structural properties of FEN enhancer oligonucleotides are conceivable for other FEN enzymes.

In a further embodiment of the confirmation assay according to the invention, the 5'-end of the target sequence-unspecific 5'-sequence of the at least one FEN probe is labelled with a detector hapten or a hapten of a specific hapten pair being sequence-specific to the matrix sequence (see Table 1).

In a further embodiment of the confirmation assay according to the invention, the reaction mixture according to the invention and described afore comprises further at least two, preferably differently, labelled FEN probes (FEN1 and FEN2, $FEN_{1-n}$), each comprising a target sequence-specific 3'-sequence, and/or at least one further primer (M1) which is complementary to a sequence fragment of a counter strand of the at least one artificial matrix sequence (see Example 1: FEN1+FEN2, FEN2+M1, Example 2, B: FEN1+FEN2; Example 3: FEN2 M1).

In a further embodiment of the confirmation assay according to the invention, the other hapten of the specific hapten pair is present as labelling at the 5'-end of the target sequence-unspecific 5'-sequence of the at least second FEN probe or of the at least one further primer (M1) (see Table 1: Can_FEN2, WB127FD).

In a further embodiment of the confirmation assay according to the invention, the amplification of the at least one artificial matrix sequence is carried out using at least one labelled 5'-cleavage product (S1, $S_{1-n}$) of the at least one FEN probe and at least one further labelled 5'-cleavage product (S2, $S_{1-n}$) of the at least second FEN probe or using at least one labelled 5'-cleavage product of the at least one FEN probe and at least one further labelled primer (M1), the labelling of the at least one artificial matrix sequence with the specific hapten pair is carried out during amplification, and at least one labelled double strand of the at least one matrix sequence amplification product having one hapten of the specific hapten pair at the respective strand is obtained.

Preferably, the labelling is carried out using one hapten of the 5'-end of the target sequence-unspecific 5'-sequence of the at least one FEN probe and the second hapten of a second FEN probe or of a further primer (M1).

According to the invention, a reaction mixture is thus preferred which comprises at least one target sequence to be verified, at least two target sequence-specific primers according to the invention (P1, P2, $P_{1-n}$), at least two FEN probes according to the invention, with their respective sequence-specific 3'-sequence being complementary to a different sequence fragment of the at least one target sequence, as exemplary shown in FIG. 1, and at least one artificial matrix sequence, wherein the at least two FEN probes are labelled with one hapten each of a specific hapten pair or only one FEN probe is labelled with one hapten of the specific hapten pair.

Preferably, the aforementioned reaction mixture comprises at least one FEN enhancer oligonucleotide (e.g. Can_ENH1, Can_ENH2, Can_ENH3 and/or Can_ENH4).

Consequently, in the confirmation assay according to the invention, the at least two FEN probes hybridize to their respective complementary sequences at the target sequence. At least two 5'-cleavage products (S1, S2, $S_{1-n}$) serving for amplification of the at least one artificial matrix sequence are obtained by cleavage of the FEN probes.

In this way, an increasingly measurable signal is measured indicating the verification of the amplified target sequence.

A specific hapten pair always consists of a detector hapten and a matrix sequence sequence-specific hapten. Specific hapten pairs are known by the person skilled in the art or may commercially be obtained from suppliers, and comprise, for example, the streptavidin-biotin-system, but also antibody-antigen pairs or hapten pairs, respectively. In particular, biotin or a biotin analogue, such as iminobiotin or desthiobiotin, as well as o-nitrophenol, peptides and/or fluorophores are suitable as detector haptens. In this context, biotin analogue is understood to mean any molecule capable of binding with streptavidin. Besides of antibodies and streptavidin, other proteinogenic receptors (English binding scaffolds) as well as aptamers (from RNA or DNA or chemical derivatives thereof, such as e.g. L-ribose, peptide nucleic acids, LNA, thiophosphate and dithiophosphate i.a.) are also known as binding partner for haptens by the person skilled in the art.

Specific hapten pairs are functionally structured such that on the one hand they recognize the substrate, presently the matrix sequence according to the invention, and on the other hand they enable a signal under the influence of the detector hapten if sequence recognition has taken place.

The detection of the signal is carried out by measurement of the matrix amplification products obtained, preferably on the basis of a color signal being visible in visible light, of an emitting fluorescence signal, of a quantum dot and/or via so-called up-converting phosphor reporter (Hampl et al. 2001). Other detection principles are known by the person skilled in the art. Preferably, colloidal particles conjugated with hapten receptors (synonymously detections colloids), such as colloidal gold or nanoparticles from latex or silicates being high-density dyed with dyes (e.g. DCN Diagnostics, Carlsbad, US-CA) as well as cellulose (e.g. NanoAct™ cellulose nanoparticles, Asahi Kasei Fibers Corp., Osaka, JP) are used as signaling material. Fluorescence signals may also be directly transferred during amplification to the at least one matrix amplification product by the 5-cleavage products ($S_{1-n}$) which carry the fluorophore as detector hapten.

The fluorescence signal comprises at least one fluorophore emitting light of a specific wave length of greater than or equal to 400 nm to less than or equal to 800 nm. Fluorescent dyes are known by the person skilled in the art and may freely be chosen in combination with the FEN probe according to the invention. Considering the detection method used, device-specific limitations are to be considered in the design of the FEN probes.

Fluorescent dyes comprise uranine, rhodamines, fluorescein, DAPI, phycoerythrin cumarins, allophycocyanin, 7-aminoactinomycin, indocyanine green/ICG, calcein, cumarin, cyanins, quinine hydrogene sulphate, fluorescein arsenical helix binder, GFP—Green Fluorescent Protein, quadrains (squaric acid dyes) based on N,N-dialkylanilins, 1,3,2-dioxaborins (complexes of boric acid derivatives with 1,3-dicarbonyl compounds), safranin, and stilbene. The person skilled in the art knows further suitable fluorescent dyes or fluorophores, respectively, and selects them from available fluorophores of current suppliers, such as biomers.net GmbH, Atto-tec GmbH, Dyomics GmbH and Thermo Fischer Scientific—Molecular Probes.

In a further embodiment of the confirmation assay according to the invention, the reaction mixture comprises at least two artificial matrix sequences differing in sequence and/or in sequence length and each comprising complementary sequences to at least one 5'-cleavage product ($S_{1-n}$) of the respective FEN probe or to at least one further primer (M1). After amplification, the matrix amplification products may differ in sequence, sequence length and/or conformation as well as, optionally, in the labelling.

In an embodiment, the reaction mixture according to the invention thus comprises
  at least one target sequence to by verified,
  at least two target sequence-specific primers (P1, P2, $P_{1-n}$) being suitable for amplification of the at least one target sequence,
  at least two FEN probes according to the invention, with their respective sequence-specific 3'-sequence being complementary to a different sequence fragment of the at least one target sequence, as exemplary shown in FIG. 1, wherein the 5'-end of the target sequence-unspecific 5'-sequence of the at least one FEN probe is labelled with a detector hapten or one hapten of a specific hapten pair being sequence-specific to the matrix sequence, and
  at least two artificial matrix sequences each comprising complementary sequences to the at least one 5'-cleavage product (S1, S2, $S_{1-n}$) of the respective FEN probe (FEN1 and FEN2), or
  at least two artificial matrix sequences, whereof one matrix sequence each comprises a complementary sequence to at least one further primer (M1) and the other to one of the two FEN probes.

In a further embodiment, the other hapten of the specific hapten pair is present at the 5'-end of the target sequence-unspecific 5'-sequence of the at least second FEN probe, preferably the FEN probes differ from one another in sequence, sequence length and/or labelling.

In a further embodiment of the confirmation assay according to the invention the reaction mixture comprises, in particular for increase of the amplification, at least quantitatively and optionally qualitatively, of the at least one artificial matrix sequence,
  at least one FEN probe according to the invention, in the manner described afore, and at least one further primer (M1),
  at least one FEN probe according to the invention (see above), at least one FEN enhancer oligonucleotide (e.g. Can_ENH1, Can_ENH2, Can_ENH3 and/or Can_ENH4), as already described above, and at least one further primer (M1), or
  at least two FEN probes according to the invention, as described above, at least one FEN enhancer oligonucleotide ($ENH_{1-n}$) and at least one further primer (M1), or
  at least two FEN probes according to the invention, at least two FEN enhancer oligonucleotides ($ENH_{1-n}$) and at least one further primer (M1), or
  at least two, preferably different, FEN probes according to the invention and at least two FEN enhancer oligonucleotides (FIG. 4, C) Can_ENH1 and Can_ENH2; D) Can_ENH3 and Can_ENH4),
wherein the at least further primer (M1) is complementary to at least one sequence fragment of the counter strand of the at least one artificial matrix sequence, and the at least second FEN probe has a target sequence-specific 3'-sequence, differing from the first FEN probe, which is complementary to a sequence within a region of the at least one target sequence being restricted by the at least first primer (P1) and the at least second primer (P2), and the cleavage product (S2) of which differs from the cleavage product (S1) of the first FEN probe and is complementary to the counter strand of the at least one artificial matrix sequence. Correspondingly, the first cleavage product (S1) is complementary to the 3'-sequence in (3' 5') of the matrix sequence. Furthermore, each of the aforementioned alternatives comprises at least one specific hapten pair for labelling of the at least one matrix sequence, wherein the hapten being sequence-specific to the matrix sequence and detector hapten is arranged on respectively different FEN probes and/or further primers (M1) (see Table 1). An example is shown in FIG. 1.

Surprisingly, it had been found in the present invention that each of the aforementioned combinations results in significant enhancement of the signal of the at least one matrix amplification product obtained, respectively compared to the signal which is obtained in the confirmation assay according to the invention with a reaction mixture with one or two FEN probes (see Table 2). Appropriate results are to be expected with the immunochromatographic method and also for hapten pair-labelled matrix amplification products and the required embodiments according to the invention for use with immunochromatographic methods, preferably NALFT. A selected embodiment for NALFT is shown in Example 2, FIG. 4. Further embodiments of the confirmation assay according to the invention are shown in Example 3, FIG. 5.

In a preferred embodiment, the combination of the at least one FEN enhancer oligonucleotide ($ENH_{1-n}$) and a further primer (M1) in the reaction mixture results in a significant enhancement of the detection signal in the confirmation assay according to the invention, preferable in at least a 30-fold enhanced signal, of the at least one, in particular labelled, matrix sequence amplification product obtained, compared to the use of one or two FEN probes, as exemplary shown for an electrophoretic method (Table 2, 900 or 931 RFU, respectively).

Figure 5:
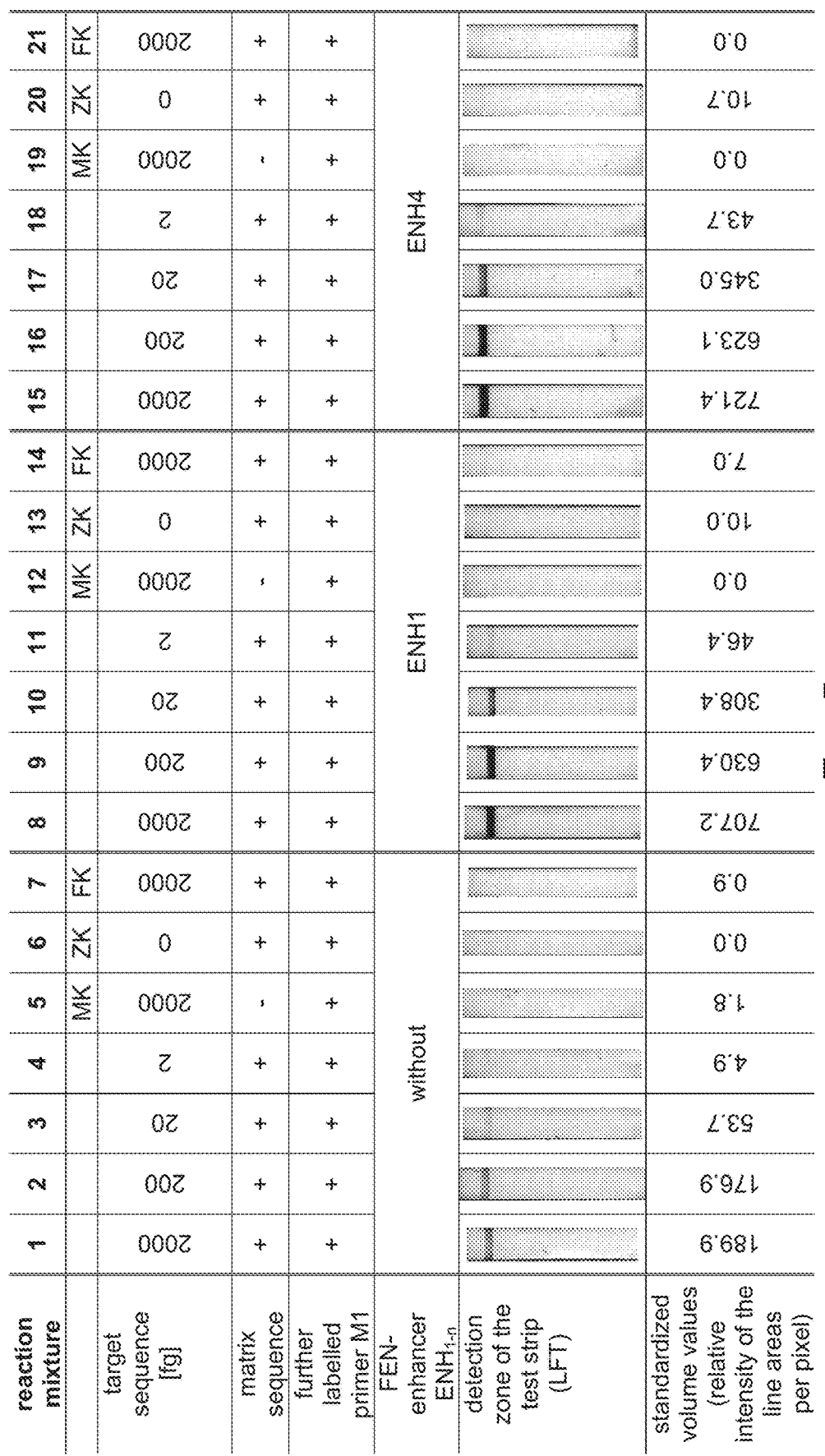

The signals achieved with the aforementioned embodiments are shown in Table 2, The combination of one labelled FEN probe and one further primer (M1) shows with a value of 5900 RFU (Table 2) compared to the confirmation test with only one or two FEN probes (900/931 RFU) a significant enhancement of the signal, a more than 6-fold enhanced signal—confirmed in Example 3, FIG. 4, The combination of one FEN probe, one FEN enhancer oligonucleotide ($ENH_{1-n}$) and one further primer (M1) results with a value of 42130 RFU in a further enhancement of the signal of the matrix amplification product (Table 2) compared to the confirmation test with only one or two FEN probes (900/931 RFU) by more than 46 fold—confirmed in Example 3, FIG. 5. Similar values are achieved with the combination of two FEN probes (FEN1 and FEN2), one FEN enhancer oligonucleotide and one further primer M1 (30747 RFU).

A combination of two FEN probes and two FEN enhancer oligonucleotides results with values of 6511 or 3500 RFU, respectively, in an up to 7-fold enhancement of the signal of the, preferably fluorescence-labelled, matrix amplification product which is detected in a capillary gel electrophoresis. The respective experimental setup with comparably good results in an immunochromatographic method is shown in Example 2 and FIG. 4.

All of the aforementioned embodiments verify the reproducibility of the confirmation test for immunochromatographic detection in the sense of the invention, which take place in a collective and continuous reaction setup for amplification of the target sequence and the amplification and optional labelling of the matrix sequence (single-tube process). Depending on the combination of FEN probe(s) with one or more FEN enhancer oligonucleotides and/or a further primer (M1), a significant enhancement of the signal is achieved. These surprising results prove the innovative solution to the assigned objective. The embodiments, in particular the combination with at least one FEN enhancer and/or a further primer (M1), provide variable solutions for a continuous reaction setup for the amplification and confirmation test of target sequences, in particular from human samples, such as blood, plasma, serum, bone and/or tissue, and reduce the risk of contamination with foreign DNA, RNA, proteins, peptides and/or chemicals. In this case, the signal has excellent quality and strength so that a simplified and improved single-tube diagnostic method including the confirmation test is provided. In particular a diagnostic method which meet the requirements according to guideline MIQ-1 2011 for nucleic acid amplification techniques and/or the guideline of the German Medical Association B3 (Rili BÄK-B3) for direct verification and characterization of infectious agents, as well as respectively meet the requirements of the respective amendments of the guidelines.

In a further embodiment of the confirmation assay according to the invention, the target sequence-specific 3'-sequences of the at least first and/or of the at least second FEN probe hybridize to their respectively complementary, in particular single-stranded, target sequence of the same molecule or to two different target sequence molecules so that complexes according to FIGS. 1 and 2 are obtained, wherein both FEN probes hybridize at the same target sequence molecule or form two different arrangements. In a first arrangement the first target sequence-specific 3'-sequence hybridizes to a first target sequence molecule and in a second arrangement the second target sequence-specific 3'-sequence hybridizes to a second target sequence molecule. Preferably, the two target sequence molecules are different and, particularly preferably, there are at least two different target sequences in one sample, in particular in one human sample according to the definition above.

In a further embodiment of the confirmation assay according to the invention, which preferably is a multiplex assay, the reaction mixture comprises at least two or more target sequences to be verified, preferably different target sequences contained in a, in particular human, sample, a combination of at least two or more FEN probes differing from one another in their sequence, sequence length and/or labelling, each being, in particular, complementary to the different target sequences, and at least two or more different artificial matrix sequences, each comprising a complementary sequence to the at least two 5'-cleavage products (S1, S2, $S_{1-n}$) of the at least two FEN probes, in particular each is a verification for at least one target sequence each, and wherein in the confirmation assay per cycle of the amplification reaction at least two or more different labelled artificial matrix sequence amplification products are obtained, each amplified target sequence is confirmed by at least one labelled artificial matrix sequence amplification product each, the at least two or more labelled artificial matrix sequence amplification products are distinctly detected and quantified in an immunochromatographic method.

In the case of two or more target sequences to be verified, two or more FEN probes differing from one another at least in the 3'-sequence are used. Furthermore, the 5'-ends of the FEN probes also differ from one another.

In particular, the multiplex kit according to the invention comprises, preferably in spatially separated arrangement or as ready for use mixture, buffer systems, nucleotides, salts etc. and any further components required for successful PCR. They are known by the person skilled in the art and/or are preset by the device manufacturers of the devices used for amplification and/or detection. Preferably, the multiplex kit according to the invention is ready for use provided for diagnostics of a, in particular human, sample.

A further subject matter of the present invention is a composition comprising a combination of at least two differently labelled target sequence-specific flap endonuclease probes (FEN probe FEN1, $FEN_{1-n}$), wherein each FEN probe respectively comprises a target sequence-specific 3'-sequence which is complementary to a sequence fragment of the at least one target sequence within a region being restricted on the target sequence by the at least first primer (P1) and the at least second primer (P2), wherein the at least two FEN probes differ from one another at least in the 3'-sequence and/or 3'-sequence length, a protective group, in particular as polymerase blocker, at the 3'-end of the target sequence-specific 3'-sequence, and a target sequence-unspecific 5'-sequence, and at least two artificial matrix sequences differing from one another at least in the sequence length by at least 10 base pairs and/or the sequence and, optionally, the labelling, wherein each of the 5'-cleavage products (S1, S2, $S_{1-n}$) of the FEN probes has a complementary sequence to one sequence fragment each of an artificial matrix sequence or of its counter strand.

Therefore, a further subject matter of the present invention is a liquid mixture comprising a PCR buffer, in particular having a suitable pH value, nucleotides, at least one (FEV1) or more FEN probes ($FEN_{1-n}$) differing from one another in their sequence, sequence length and/or labelling, and each FEN probe comprises a target sequence-specific 3'-sequence which is complementary to a sequence fragment of at least one target sequence within a region being restricted by at least one first primer (P1) and at least one second primer (P2), a protective group, in particular as polymerase blocker, at the 3'-end of the target sequence-specific 3'-sequence, preferably the 3'-OH group is missing, and a target sequence-unspecific 5'-sequence, and at least one or more different artificial matrix sequences differing in their sequence and/or sequence length and each comprising complementary sequences to at least one 5'-cleavage product (S1, $S_{1-n}$) of at least one FEN probe or to at least one further primer, and optionally, supplements and additives being known by the person skilled in the art.

The confirmation assay according to the invention as well as the multiplex kit according to the invention preferably is a method and/or kit for diagnosis and confirmation of the diagnosis of bacteria, parasites, fungi and/or viruses. In particular for verification of *chlamydia, streptococcus, legionella, listeria*, MRSA, mycobacteria, *salmonella, toxoplasma, candida*, hepatitis, HIV, influenza, varicella zoster, parvovirus and/or enteroviruses.

Thus, a further subject matter of the present invention is a confirmation assay, wherein, in particular, the reaction mixture comprises at least two labelled, preferably different, FEN probes (FEN1, FEN2, $FEN_{1-n}$) or at least one FEN probe and at least one further primer (M1), the amplification of at least one artificial matrix sequence is carried out with at least one 5'-cleavage product (S1, $S_{1-n}$) of the at least one FEN probe (FEV1) and at least one further 5'-cleavage product of the at least second FEN probe (FEN2) or at least one further primer (M1), the labelling of the at least one artificial matrix sequence is carried out during amplification, wherein the matrix sequence amplification product is labelled with a specific hapten pair, and at least one labelled double strand of the at least one matrix sequence amplification product is obtained, which has one hapten of the specific hapten pair at the respective strand, and in particular the hapten pair-labelled matrix sequence amplification product is distinctly detected at a solid phase. In particular within a defined detection zone of a solid phase, preferably within a detection zone of a lateral flow testing strip as shown in FIG. 4.

An amplification product-specific (synonymous=specific) hapten pair, in particular for a NALFT, is understood to mean the combination of two haptens with a specific double-stranded DNA amplification product. In this case, the respective haptens of the specific hapten pair are specifically connected (or "bridged") to one another via the stable DNA double helix and cause a measurable signal through their binding.

The essential difference of the confirmation assay according to the invention to the state of the art is that the at least one hapten pair-labelled artificial matrix sequence amplification product obtained is the confirmation (synonymous=verification) of at least one amplified target sequence to be verified. If the hapten pair-labelled artificial matrix sequence amplification product may be verified or measured in any way, the confirmation test was successful.

Therefore, a further subject matter of the present invention is the at least one labelled artificial matrix sequence amplification product which has been labelled by the at least two 5'-cleavage products (S1, S2, $S_{1-n}$) of the at least two FEN probes or which has been labelled by the 5'-cleavage product of the at least one FEN probe and the at least one labelled further primer (M1), in particular as confirmation of at least one amplified target sequence.

Therefore, a further subject matter of the present invention is at least one hapten pair-labelled artificial matrix sequence amplification product, in particular obtained or obtainable in a confirmation assay according to the invention.

In a preferred embodiment of the confirmation assay according to the invention, the at least one artificial matrix sequence amplification product labelled with a hapten pair, in particular obtained from the upstreamed amplification, is detected via an immunochromatographic method, preferably via a nucleic acid lateral flow (HALF) immunochromatographic method.

The hapten pair-labelled artificial matrix sequence amplification product may immediately be supplied to a detection method, or may be detected location-independently at a later time. Thus, the hapten pair-labelled artificial matrix sequence amplification product obtained may be stored. The confirmation assay according to the invention may be performed at the Point-of-Need and the detection may be carried out at a location having appropriate resources (e.g. availability of a thermocycler or isothermal processor as well as of NALF-testing strips).

Preferably, in the confirmation assay according to the invention, a suitable buffer is immediately added to the at least one hapten pair-labelled artificial matrix sequence amplification product, and the mixture obtained is immediately supplied to the immunochromatographic method, in particular brought into contact with a solid phase. Preferably, a lateral flow running buffer is immediately added, and the mixture obtained is applied to a sample application region of a lateral flow testing strip.

In a preferred embodiment of the confirmation assay according to the invention, the at least one hapten pair-labelled artificial matrix sequence amplification product is detected through the use of a signal which is emitted by a fluorescing and/or by a compound being measurable in visible light. The hapten pair-labelled artificial matrix sequence amplification product thereby initiates the respective reaction of at least one pre-compound into the respectively measurable compound. Preferably, the at least one pre-compound is processed into a signal-emitting compound, in particular enzymatically cleaved and/or stimulated by influence of a light source.

In a further embodiment of the confirmation assay according to the invention, the reaction mixture comprises
- greater than one to less than or equal to 10 different FEN probes correspondingly being labelled with one hapten each of the greater than one to less than 10 different specific hapten pairs, and
- greater than one to less than or equal to 10 different artificial matrix sequences.

In a particular embodiment of the confirmation assay according to the invention, a combination of greater than one to less than or equal to 10, preferably two, three, four, five, six, seven, eight, nine or ten, different matrix sequence amplification products labelled with one specific hapten pair each are confirmed in a collective and continuous reaction mixture, and are simultaneously and distinctly detected via an immunochromatographic method at a solid phase. Preferably, greater than or equal to 2 to less than or equal to 10 hapten pair-labelled artificial matrix sequence amplification products are detected within a defined detection zone of a solid phase, preferably of a lateral flow testing strip. In this context, the hapten pair-labelled artificial matrix sequence amplification products differ in the combination of different specific hapten pairs, the sequence, sequence size and/or conformation of the hapten pair-labelled artificial matrix sequence amplification products. Up to 10 target sequences may be confirmed in a detection zone of a testing strip by suitable choice of different specific hapten pairs and artificial matrix sequences.

The confirmation assay according to the invention, preferably using a solid phase for detection of the signal of the at least one hapten pair-labelled matrix sequence amplification product, comprises the steps of
- interaction of the at least one mobile hapten pair-labelled matrix sequence amplification product, in particular being in a buffer, with a receptor molecule of the detector hapten via the detector hapten, wherein the receptor molecule is conjugated to a detection colloid of a signal-generating pre-compound, and, simultaneously, adheres as instant-preparation (instant-preparation comprises fillers and/or stabilizers etc.) in a predefined depot region (conjugate zone) of a solid phase alternatively, the detector hapten may also be a fluorophore, which may directly by verified by a fluorescence reader
- obtaining of a mobile matrix sequence amplification product/receptor molecule/detection signal compound complex
- interaction of the at least one mobile aforementioned complex with a specific immobilized receptor molecule via the sequence specific hapten still available, and
- detection of a measurable signal, in particular in a detection zone (synonymous=detection field) of a solid phase, preferably of a testing strip, as shown in FIG. 4.

The reproducibility of the assay according to the invention using a solid phase in the detection method, preferably of a lateral flow testing strip, is described in Example 2 and 3 and shown in FIGS. 4 and 5. A distinct band was detected at the upper edge of the detection zone, which represents the hapten pair-labelled matrix sequence amplification product and thus confirms the target sequence amplification product. Thereby, the functionality and reproducibility of the present invention is also excellently proved for methods using a solid phase in the detection method, preferably a lateral flow testing strip. A more visible band is detected (FIGS. 4 C and D; FIG. 5 reaction mixtures 8-11 and 15-18) by suitable choice of FEN enhancer oligonucleotides (Can_ENH1, Can_ENH2, Can-ENH3 and/or Can-ENH4). Below the bands visible in FIG. 3 or 5, further target sequence amplification products may be distinctly detected and confirmed on the basis of bands detectable underneath, using more than two artificial matrix sequence amplification products and suitable specific hapten pairs.

A further subject matter of the present invention is a multiplex kit, in particular for use in the confirmation assay according to the invention, comprising a combination of
- at least one labelled (FEN1) or more labelled FEN probes (FEN$_{1-n}$) differing from one another, in particular in their sequence, sequence length and/or labelling, and each FEN probe comprises
  - a target sequence-specific 3'-sequence which is complementary to a sequence fragment of the at least one target sequence within a region being restricted on the target sequence by the at least first primer (P1) and the at least second primer (P2),
  - a protective group, in particular as polymerase blacker, at the 3'-end of the target sequence-specific 3'-sequence, preferably the 3'-OH group is missing, and
  - a target sequence-unspecific 5'-sequence which is labelled at its 5'-end with a detector hapten or one hapten of a specific hapten pair being sequence-specific to the matrix sequence, and
- at least one or more different artificial matrix sequences differing in their sequence and/or in their sequence length and each comprising complementary sequences to at least one 5'-cleavage product (S$_{1-n}$) of the at least one FEN probe or to at least one further primer (M1).

In a further embodiment of the multiplex kit according to the invention, it comprises at least two labelled FEN probes (FEN1 and FEN2, FEN$_{1-n}$) and/or at least one labelled FEN probe and at least one further labelled primer (M1), whereby one hapten each of a specific hapten pair is present as labelling.

In a further embodiment of the multiplex kit according to the invention, the other hapten of the specific hapten pair is present as label at the 5'-end of the target sequence-unspecific 5-sequence of the at least second FEN probe or at the at least one further primer (M1) (see e.g. Table 1).

Preferably, the multiplex kit according to the invention comprises the reaction mixture described afore, in particular as ready to use mixture for use in the confirmation assay according to the invention, and any supplements required for a PCR, such as e.g. puffer systems, nucleotides, salts, etc., which are known by the person skilled in the art.

In an embodiment of the confirmation assay according to the invention, the haptens are arranged,
- according to an alternative, one hapten at the 5'-end of the target sequence-unspecific 5'-sequence of the at least one FEN probe FEN1 and the other hapten at at least one further primer (M1) (see Table 1), or according to another alternative, one hapten each respectively on a first and a second FEN probe each (FEN1 and FEN2) (see Table 1), and these ones respectively label in common the at least one matrix sequence amplification product with the specific hapten pair, and in particular for obtaining of at least one hapten pair-labelled artificial matrix sequence amplification product and in particular for detection of the aforementioned matrix sequence amplification product at a solid phase.

DESCRIPTION OF THE FIGURES (FIG.)

FIG. 1: Relative arrangement of PCR-primers, FEN probes, FEN enhancer oligonucleotides and additional primers used. A) The relative binding sites of the PCR primers (Can_Set003_SP11, Can_Set002_ASP1), FEN probes (Can_ FEN1, Can_FEN2) and FEN enhancer oligonucleotides (Can_ENH1-4) relating to the 18S rDNA region of C. albicans are shown. The strand corresponds to gene bank access number AY497754. X stands for hapten 2, Y stands for 6-carboxyfluorescein or hapten 1. B) The target sequence-unspecific 5'-sequence regions (dotted arrows) of the FEN probes Can_FEN1 and Can_FEN2 bind after their cleavage to the artificial matrix sequence Alpha 1. The DNA sequence of primer WB127, unlabelled (WB127F), optionally labelled with a hapten (WB127FD), is identical to the cleaved 5'-sequence region of the FEN probe Can_FEN1. The figures are not shown to scale. Polymerase blockers (3'-C3-carbon spacer) are shown as diamonds. 3'-nucleotides of the FEN enhancer oligonucleotides ($ENH_{1-n}$), which overlap with the target sequence-specific regions of the FEN probes, are shown as open circles. Arrows refer to oligonucleotides which may be function as primer.

FIG. 2: Hybridisation of FEN probes (Can_FEN1, 2) and FEN enhancer oligonucleotides (Can_EHN1-4) with their target sequences. A) The sequences of Can_FEN1 (SEQ ID NO: 3) and of the corresponding FEN enhancer oligonucleotides Can_ENH1 (SEQ ID NO: 9) and Can_ENH3 (SEQ ID NO: 10) are shown. B) The sequences of Can_FEN2 (SEQ ID NO: 4) and the corresponding FEN enhancer oligonucleotides Can_ENH2 (SEQ ID NO: 8) and Can_ENH4 (SEQ ID NO: 11) are shown. The target sequences (SEQ ID NOs: 13 and 14) correspond to subsequences of the counter strand of the 18s rDNA region of C. albicans having gene bank access number AY497754. X, unlabelled or hapten 2; Y, 6FAM, 6-'carboxyfluorescein or hapten 1; spacer 3, polymerase blocker 3'-C3 carbon spacer.

Figure 3B:
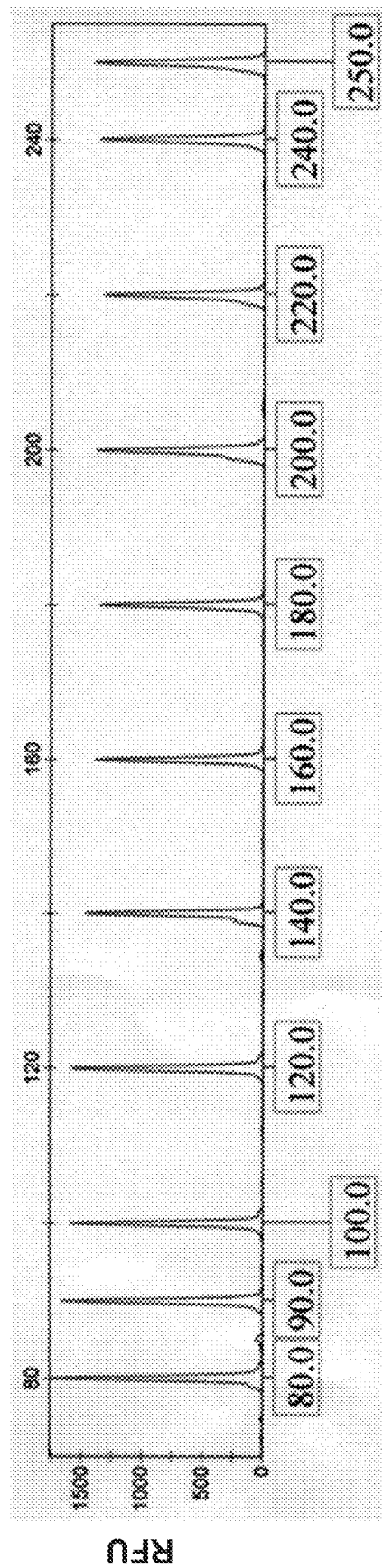

FIG. 3: Analysis of an artificial amplification product which was formed as a function of the cleavage product of the FEN probe Can_FEN2 via the Applied Biosystems® 3500 Genetic Analyzer. The PCR was composed of 50 pg genomic DNA of C. albicans, PCR primers Can_Set003_SP11 and Can_Set002 ASP1, the 5'-6FAM-labelled FEN probe Can_FEN2, the FEN enhancer oligonucleotide Can_ENH2, the addition unlabelled primer WB127F and the artificial matrix sequence Alpha 1. Further details see text. An aliquot of 1 µL of a 1:20 dilution of the PCR amplification product was analyzed. A) 6FAM-analysis channel with the amplification product of Alpha 1. B) Size standard in the analysis channel BTO. RFU, relative fluorescence units.

FIG. 4: Verification of PCR amplification products via lateral flow (LF) immunochromatography testing strips (LFT). The functional structure of the LFT is explained on the left margin. An arrow on the right margin marks the specific detection line. The PCR was performed with genomic DNA of C, albicans, the primer pair Can_Set003_SP11 and Can_Set002_ASP1 as well as the 5'-hapten-labelled FEN probe pair Can_FEN1 and Can_FEN2 and the artificial matrix sequence Alpha 1, as described in Example 1. A) Negative control without genomic DNA. B) Complete PCR without additional FEN enhancer oligonucleotides. C) Complete PCR, additionally with FEN enhancer oligonucleotides Can_ENH1 and Can_ENH2, D) Complete PCR, additionally with FEN enhancer oligonucleotides Can_ENH3 and Can_ENH4.

FIG. 5: Verification of PCR amplification products via LFT as a function of the content of the target sequence to be verified. The functional structure of the LFT is already shown and explained in FIG. 4, such that only the detection zone of the respective LFT is shown in FIG. 5. The PCR was performed with genomic DNA of C. albicans as target sequence to be verified, the primer pair (P1, P2) Can_Set003_SP11 and Can_Set002_ASP1, the 5'-hapten 1-labelled FEN probe Can_FEN2, the 5'-hapten 2-labelled additional primer (M1) WB127FD and, optionally, in combination with a FEN enhancer oligonucleotide Can_ENH1 or Can_ENH4 and the artificial matrix sequence Alpha 1, as described in Example 1. The aforementioned reaction mixture without target sequence (ZK), the aforementioned reaction mixture without matrix sequence (MK) and the aforementioned reaction mixture with a KlenTaq DNA polymerase lacking FEN activity (FK) instead of a DNA Taq DNA polymerase were used as controls.

In the following, selected examples show ways for achievement of the solution according to the invention are explained, wherein the examples presented herein are not to be construed restrictively.

EXAMPLES

Example 1: Confirmation of a PCR Amplification Product Using a Flap Endonuclease (FEN) Probe and an Artificial Matrix Sequence with the Applied Biosystems® 3500 Genetic Analyzer Material and Methods DNA Purification from *Candida albicans* DSM 1386:

The reference strain was obtained from DSMZ—German Collection of Microorganisms and Cell Cultures GmbH (Braunschweig, DE), Yeast cells were cultivated on Sabouraud glucose agar with chloramphenicol (Bio-Rad Laboratories GmbH, München, DE) at 25° C. The cells were harvested with a sterile spatula and resuspended in sterile phosphate-buffered salt solution (PBS, 137 mM NaCl, 2.7 mM KCl, 10 mM $Na_2HPO_4$, 1.8 mM $KH_2PO_4$, pH 7.4). The DNA purification was carried out with the QIAamp® DNA Mini Kit (Qiagen GmbH, Hilden, DE) according to manufacturer's specifications and the following modification: The samples were mixed with ATL buffer and proteinase K of the manufacturer for cell disruption and incubated at 50° C. for at least 12 h. The purified DNA was quantified may means of UV-VIS spectroscopy using an Eppendorf® BioPhotometer® (Eppendorf AG, Hamburg, Germany).

Design and Synthesis of PCR Primers, FEN Probes, FEN Enhancer Oligonucleotides and the Universal Matrix Sequence:

A part of the 18s rDNA gene of C. albicans (gene bank accession number AY497754) was selected as target sequence. A 127-base artificial matrix sequence Alpha 1 was partly derived from the lacZα-sequence of the pUC19 plasmid (gene bank accession number L09137). PCR primers, FEN probes and FEN enhancer oligonucleotides were designed using the software Vector NTI® (Thermo Fisher Scientific Inc.—Life Technologies Div., Darmstadt, DE) and Mfold (Zuker 2003). The primer binding temperatures ($T_a$) of FEN probes (Can_FEN1 and Can_FEN2) and FEN enhancer oligonucleotides (Can_ENH1, Can_ENH2, Can_ENH3, Can_ENH4) were set at least 5° C. higher than the $T_a$ of the PCR primers, similarly to the design rules for hydrolysis probes (Heid et al. 1996).

Oligonucleotides which overlapped at the 3'-end with one (Can_ENH3, Can_ENH4) or two (Can_ENH1, Can_ENH2) nucleotides to the target sequence-specific 5'-binding site of the FEN probe and additionally contained a not-pairing base (3'-flap) at their 3'-end were designed 3'-upstream the FEN probes as FEN enhancer oligonucleotides (Lyamichev et al. 1993, Xu et al. 2001) (FIG. 2).

The relative arrangement of PCR primers, FEN probes and FEN enhancer oligonucleotides on the target sequence is shown in FIG. 1. FIG. 2 shows the DNA sequence of FEN probes and FEN enhancer oligonucleotides as well as their binding sites on the target DNA.

All oligonucleotides were obtained in HPLC-purified quality from biomers.net GmbH (Ulm, DE).

Polymerase Chain Reaction (PCR):

The PCR was performed in a volume of 25 µL and contained 1×REMA buffer (with final concentrations of 0.2 mM dNTPs and 1.5 mM MgCl2; Biotype Diagnostic GmbH, Dresden, DE), 2.5 units Multi Taq2 DNA polymerase (with hotstart function; Biotype Diagnostic GmbH, Dresden, DE), 10-50 pg chromosomal DNA of C. albicans, 4 nM to 4 µM artificial matrix sequence Alpha 1, 0.3 µM PCR primers and 0.3 µM FEN probe Can_FEN2 having 5'-6FAM-labelling. The unlabelled FEN probe Can_FEN2, FEN enhancer oligonucleotides and/or primer WB127F were optionally also used in a final concentration of 0.3 µM (DNA sequences see Table 1 and 2).

Zero controls were performed without chromosomal DNA of C. albicans. Additionally, experiments were performed on KlenTaq1, an N-terminal deletion variant of the Taq DNA polymerase lacking FEN activity (U.S. Pat. No. 5,436,149; DNA Polymerase Technology Inc., St. Louis, US-MO). An Eppendorf MasterCycler® ep Gradient Thermal Cycler (Eppendorf AG, Hamburg, DE) was used. The temperature change consisted of 4 min of hotstart activation at 96° C. and 35 cycles of 30 s at 96° C., 60 s at 60° C. and 60 s at 72° C. Finally, an elongation step was performed at 72° C. for 10 min, and the reaction setups were subsequently stored at 4° C. until further analysis.

Capillary Gel Electrophoresis Using the Applied Biosystems® 3500 Genetic Analyzer (Thermo Fisher Scientific—Applied Biosystems Div., Foster City, US-CA):

The analyzer was used with the 3500 POP-7™ Polymer (Performance Optimized Polymer) according to manufacturer's specifications and with the following adjustments: The spectral calibration of the device was carried out using the virtual filter set Any5Dye in combination with matrix standard BT5 (fluorescent dyes 6FAM, BTG, BTY, BTR, BTO, for blue, green, yellow, red and orange) (Biotype Diagnostic GmbH, Dresden, DE). Aliquots of 1 µL of the PCR or of dilutions thereof, respectively, were mixed with 12 µL HiDi Formamide (Thermo Fisher Scientific—Applied

TABLE 1

Primers, FEN probes, FEN enhancer oligonucleotides and artificial matrix sequence. The primer binding temperature ($T_a$) was calculated using the software Vector NTI ® (Thermo Fisher Scientific Inc.-Life Technologies, Darmstadt, DE) using the standard settings. Underlined sequences correspond to the 5'-ends of the flap endonuclease (FEN) probes binding as PCR primer to the artificial matrix sequence Alpha 1 or its counter sequence after cleavage.
6FAM, 6-carboxyfluorescein; X = unlabelled or hapten 2, Y = 6FAM or hapten 1, Spacer 3 = 3'-C3 carbon spacer.

| name | sequence (5'→3'-end) and modification | $T_a$ [° C.] |
|---|---|---|
| Can_Set003_SP11 | GGTAGGATAGTGGCCTACCATGGTTT (SEQ ID NO: 1) | 58.7 |
| Can_Set002_ASP1 | CCGACCGTCCCTATTAATCATTACGAT (SEQ ID NO: 2) | 60.4 |
| Can_FEN1 | X-TTAACTATGCGGCATCAGAGCAGATTGGAGGGCAAGTCTGGT GCCAGC-Spacer 3 (SEQ ID NO: 3) | 66.9 |
| Can_FEN2 | Y-CAACAGTTGCGCAGCCTGAATGCGTACTGGACCCAGCCGAG CC-Spacer3 (SEQ ID NO: 4) | 67.7 |
| WB127F | TTAACTATGCGGCATCAGAGCAGA (SEQ ID NO: 5) | 57.8 |
| WB127FD | Hapten2-TTAACTATGCGGCATCAGAGCAGA (SEQ ID NO: 6) | 57.8 |
| Can_F1 | AACCTTGGGCTTGGCTGGC (SEQ ID NO: 7) | 58.6 |
| Can_ENH2 | CTTGGCTGGCCGGTCCATCTTTTTGAG (SEQ ID NO: 8) | 68.0 |
| Can_ENH1 | TTGGAATGAGTACAATGTAAATACCTTAACGAGGAACAAG (SEQ ID NO: 9) | 66.0 |
| Can_ENH3 | TTGGAATGAGTACAATGTAAATACCTTAACGAGGAACAG (SEQ ID NO: 10) | 65.4 |
| Can_ENH4 | CTTGGCTGGCCGGTCCATCTTTTTGG (SEQ ID NO: 11) | 66.8 |
| Alpha1 | TTAACTATGCGGCATCAGAGCAGATTGTACTGAGAGTGCACCAT ATGCGGTGTGAAATACCGCACAGATGCGTAAGGAGAAAATACC GCATCAGGCGCCATTCGCCATTCAGGCTGCGCAACTGTTG (SEQ ID NO: 12) | nonapplicable |

Biosystems Div., Foster City, US-CA) and 0.5 µL size standard SST-BTO (Biotype Diagnostic GmbH, Dresden, DE), incubated at 95° C. for 3 min, and subsequently stored at room temperature in the automatic sampler of the device until electrokinetic injection (10.000 V, 5 s). The analysis unit of the analyzer records relative fluorescence units (RFU) against the fragment length (bases, b) (see FIG. 3). The device configuration maximally allows for semi-quantitative analysis (up to 20% variation between the injections of the same samples).

Results and Discussion

At first, the optimal primer binding temperature $T_a$ of 60° C. for the C. albicans PCR and the PCR primer pair Can_Set003_SP11 and Can_Set002_ASP1 was determined in a $T_a$-gradient between 55° C. and 65° C. A specific band corresponding to the calculated length of 539 bp could be visualized via ethidium bromide staining after agarose gel electrophoresis (not shown). Thereafter, the optimal concentration for the universal DNA matrix Alpha was determined in PCRs which contained 0.3 µM of FEN probe Can_FEN2 having 6FAM-labelling at the 5-end and 4 nM to 4 µM of the artificial matrix sequence Alpha1 additionally to the PCR primer pair. The results were evaluated via Applied Biosystems® 3500 Genetic Analyzer.

A dilution between 20 nM to 160 nM gave good results.

and the primer WB127F surprisingly resulted in approximately 34-46-fold higher signals.

Example 2: Confirmation of a PCR Amplification Product Using Two FEN Probes, an Artificial Matrix and a Lateral Flow Immunochromatography Testing Strip Material and Methods Chromosomal DNA and oligonucleotides:

DNA purification from C. albicans DSM 1386 and design and synthesis of the oligonucleotides were already described in Example 1 (see also Table 1).

PCR:

The PCR was performed as described in Example 1, but using two FEN probes, Can_FEN1 labelled with hapten 2 at the 5'-end and Can_FEN2 labelled with hapten 1 at the 5'-end. The further primer (M1), WB127 (unlabelled or with hapten 2), was not used. Primers, FEN probes and FEN enhancer oligonucleotides were also used in final concentrations of 0.3 µM. The final concentration of the artificial matrix sequence Alpha 1 was 40 nM. PCR thermocycler and PCR program were identical with Example 1.

Verification of Nucleic Acid Amplification Products Via Lateral Flow (LF) Immunochromatography Testing Strips (LFT):

TABLE 2

Analysis of the PCR products with the Applied Biosystems ® 3500 Genetic Analyzer.
All PCR were performed with 50 pg chromosomal DNA of C. albicans, 40 nM Alpha 1,
0.3 µM Can_Set003_SP11 and 0.3 µM Can_Set002_ASP1. 1 µL each of a 1:20 dilution
of the PCR amplification products was used. RFU, relative fluorescence units of the signal areas.

FEN probes, FEN enhancer oligonucleotides and additional primer (M1)
WB127F (final concentrations 0.3 µM)

| RFU | Can_FEN1 | Can_FEN2 | Can_ENH1 | Can_ENH2 | Can_ENH3 | Can_ENH4 | (M1) WB127F |
|---|---|---|---|---|---|---|---|
| 900 | − | + | − | − | − | − | − |
| 8661 | − | + | − | + | − | − | − |
| 4954 | − | + | − | − | − | + | − |
| 5900 | − | + | − | − | − | − | + |
| 42130 | − | + | − | + | − | − | + |
| 30747 | + | + | − | − | − | + | + |
| 931 | + | + | − | − | − | − | − |
| 6511 | + | + | + | + | − | − | − |
| 3500 | + | + | − | − | + | + | − |

Subsequently, PCRs were performed always containing 40 nM Alpha 1 and 0.3 µM of FEN probe Can_FEN2 having 5'-6FAM-labelling. Additionally, the unlabelled FEN probe Can_FEN1, FEN enhancer oligonucleotides and/or the primer WB127F binding to the 5'-end of the Alpha 1 counter strand (see also FIG. 1 and Table 1) were tested in certain PCRs. The results are summarized in Table 2. The 127 bp amplification product which was expected with the artificial matrix sequence Alpha 1 could be confirmed (FIG. 3). Control setups without genomic DNA or with the KlenTaq1 DNA polymerase instead of the Taq DNA polymerase did not show any amplification products (not shown). Amplification of the artificial matrix sequence Alpha 1 was thus dependent on the FEN activity of the Taq DNA polymerase.

As shown in Table 2, the signal could not essentially be increased by the addition of a second FEN probe, whose 5'-cleavage product binds to the 5'-end of the Alpha 1 is counter strand. Approximately 5.5-6.5-fold higher signals could be achieved by the sole addition of FEN enhancer Can_ENH2 or Can ENH4. The addition of a FEN enhancer Components and reagents of a contract manufacturer were used. Usually, contract manufacturers protect the precise chemical composition of the LF running buffer and the structure of the LFTs (haptens and their receptor molecules) as trade secrets and do not disclose them. However, for reproducibility the components may be obtained from the manufacturer in combination with customer-specific hapten labelled oligonucleotides (e.g. Amodia Bioservice GmbH, Braunschweig, DE), The structure of the strip used is shown in FIG. 4. It has a detection zone being functionalized in lines with hapten-specific receptor molecules (mostly monoclonal antibodies). The LFT strip used had 5 different functionalized lines in the detection region. Hapten 1 whose receptor molecule was furthest from the dipping zone was used. The conjugate region contained nanogold particles dried with stabilizers which were functionalized with a second receptor molecule (here for hapten 2). The correspondingly labelled FEN probes are shown in Table 1 and FIG. 1.

Aliquots of 5 µL of the PCR amplification products were mixed with 100 µL LF running buffer in a 1.5 mL reaction vessel. The LFT was subsequently dipped into the reaction setup and chromatographically developed at room temperature for 20 min. The results were evaluated by eye.

Results and Discussion

The results are shown in FIG. 4. Compared to the zero control, only a negative to weakly positive result could be achieved by using the two FEN probes solely. The addition of FEN enhancer oligonucleotides resulted in a clear signal increase, wherein the combination of Can_ENH1 and Can_ENH2 gave the best results.

Example 3: Confirmation of a PCR Amplification Product Using a Hapten-Labelled FEN Probe, in Combination with a Further Hapten-Labelled Primer (M1) and a FEN Enhancer Oligonucleotide (ENH) Via a Lateral Flow Immunochromatography Testing Strip (LFT)

Material and Methods

Chromosomal DNA and oligonucleotides:

DNA purification from *C. albicans* DSM 1386 and design and synthesis of the oligonucleotides were already described in Example 1 (see also Table 1).

PCR:

The PCR was performed analogously to the PCR of Example 1, but using the FEN probe labelled with hapten 1 at the 5'-end, Can_FEN2, and a further primer (M1) labelled with hapten 2 at the 5'-end, WB127FD. Primer, FEN probe and FEN enhancer oligonucleotide were also used in final concentrations of 0.3 μM each. The final concentration of the artificial matrix sequence Alpha 1 was 40 nM, Different DNA amounts of the target sequence to be verified, 2000 fg, 200 fg, 20 fg and 2 fg chromosomal DNA of *C. albicans*, were added. PCR thermocycler and PCR program were identical with Example 1.

a) a PCR without target sequence to be verified (ZK in FIG. 5: reaction mixtures 6, 13 and 20), b) a PCR without artificial matrix sequence (MK in FIG. 5: reaction mixtures 5, 12, 19), and c) a PCR with 2.5 units KlenTaq1 DNA polymerase (DNA Polymerase Technology Inc., St. Louis, US-MO) lacking FEN activity (FK in FIG. 5: reaction mixtures 7, 14, 21) served as controls.

Verification of Nucleic Acid Amplification Products Via Lateral Flow (LF) Immunochromatography Testing Strips (LFT):

Verification was carried out as described in example 2. Additionally, the LFT were analyzed using the LF reader opTrilyzer® (opTricon GmbH, Berlin, DE). The analysis software opTrilyzer® Data Viewer of the reader determines standardized volume values from the pixel intensities of the test line areas of its CCD camera (relative intensity of the line areas per pixel) (see FIG. 5). The manufacturer defines a device-specific detection limit of 10 standardized volume values.

Results and Discussion

The results are shown in FIG. 5. The controls without target sequence (ZK, FIG. 5, reaction mixtures 6, 13 and 20), without artificial matrix sequence Alpha 1 (MK, FIG. 5, reactions mixtures 5, 12 and 19) and with KlenTaq1 DNA polymerase (FK, FIG. 5, reaction mixtures 7, 14 and 21) showed no bands, as expected. This proves the selectivity of the confirmation assay according to the invention.

Compared to Example 2 (see FIG. 4, LFT B), in which no target sequence (starting content 50 pg) could be verified with two FEN probes without FEN enhancer oligonucleotide and without further primer M1, low amounts of the target sequence could successfully be verified with a combination of a FEN probe and a further labelled primer (M1), WB127FD, even without FEN enhancer oligonucleotide (FIG. 5, reactions mixtures 1-3).

Surprisingly, the target sequence with a starting content of 2000 fg, 200 fg and even only 20 fg, being lower by a factor 25, 250 and even 2500 compared to Example 2 (50 ng), was successfully verified on the basis of a distinct Band on the LFT which is visible by the human eye (FIG. 5, reaction mixtures 1, 2 and 3).

These results confirm the results achieved in Example 1 via the Applied Biosystems for the combination of a FEN probe and a further Primer M1 without FEN enhancer oligonucleotide (Table 2, 5900 RFU) and show that already one FEN probe is sufficient for successful and unequivocal verification of low DNA amounts of the target sequence, even with the naked eye.

The reaction mixtures of Examples 1, 2 and 3 used in the confirmation assay according to the invention are summarized in following Table 3.

TABLE 3

Overview of the reaction mixtures according to the invention (respectively based on a total volume of 25 μl)

| reaction mixture | Example 1 | Example 2 | Example 3 |
|---|---|---|---|
| amount of the target sequence to be verified (*C. albicans*) | 50 pg | 50 pg | 2000/200/20/2/0 fg |
| primers (P1, P2) | Can_Set003_SP11 Can_Set002_ASP1 0.3 μM each | | |
| FEN probe(s) (FEN$_{1-n}$) | Can-FEN1 Can-FEN2 0.3 μM each | Can-FEN1 Can-FEN2 0.3 μM each | Can-FEN2 ./. 0.3 μM |
| number of FEN$_{1-n}$ | 1 or 2 | 2 | 1 |
| Artificial matrix sequence | Alpha 1 40 nM | | |
| further primer (M1) | WB127F 0.3 μM | without | WB127FD 0.3 μM |
| FEN enhancer oligonucleotide (ENH$_{1-n}$) | Can_ENH2 or Can_ENH4 or Can_ENH/ Can_ENH2 or Can_ENH3 + ENH4 0.3 μM each | ./. ./. Can_ENH1/ Can_ENH2 or Can_ENH3 + ENH4 0.3 μM each | Can_ENH1 or Can_ENH4 ./. ./. 0.3 μM each |
| number of ENH$_{1-n}$ | 1 or 2 | 0 or 2 | 0 or 1 |

With the addition of a FEN enhancer oligonucleotide (ENH1 or ENH4), a target sequence having even a starting content of only 2 fg could successfully be verified on the basis of a distinct band (FIG. 5, reaction mixtures 11 and 18). This means that, the confirmation assay according to the invention, whose reproducibility has already been shown in Examples 1 and 2, again achieves a sensitivity being higher by a factor of 25000 in comparison with Example 2 (50 pg to 2 fg).

The results of Example 3 (FIG. 5, reaction mixtures 8-11, 15-18) confirm the results achieved in Example 1 via the Applied Biosystems for the combination of a FEN probe and one further Primer M1 and one FEN enhancer oligonucleotide at a starting content of the target sequence of 50 pg (Table 2, 45130 RFU), and additionally prove a successful and unequivocal verification of very low DNA amounts of the target sequence to be verified (20 fg or 2 fg, respectively), even with the naked eye, using the aforementioned reaction mixture.

Visual analysis with the naked eye as well as display of distinct bands in the detection zone of the LFT after scanning the LFT clearly prove the functionality of the reaction mixture and the confirmation assay according to the invention.

A detection limit of 2 fg starting material of the target sequence to be verified of *C. albicans* could reproducibly be shown via a lateral flow reader calibrated for diagnostic purposes (FIG. 5, reaction mixtures 11 and 18; cutoff 20 standardized volume values).

*C. albicans* has a diploid genome with an average of 29.2 Mb (megabase pairs) (Hirakawa et at 2015) and plus approximately 48 copies of mitochondrial DNA (mtDNA) with approximately 0.04 Mb (Fukuoh et al, 2014). Thus, one cell of *C. albicans* contains approximately 31.1 Mb DNA. Since 1 fg of double-stranded DNA corresponds to 0.978 Mb (Dolezel et al, 2003), approximately 32 fg DNA content per cell are calculated for the yeast cell. Fungi have approximately 20-200 copies of 18s rDNA genes per genome which were used as target sequence in the test Thus, it can be concluded that surely one cell and very likely at least 10 copies of the target sequence to be verified constituting the stochastic lower limit of a practicable laboratory test were verified with the assay according to the invention using the *C. albicans* target sequence with multiple copies per genome.

The above conversion is transferable to each genome and thus to any other target sequence to be verified, preferably DNA, Consequently, a further subject matter of the present invention is a confirmation assay of the manner described herein in which the content of the at least one target sequence to be verified, in particular DNA, preferably double-stranded DNA, particularly preferably of a target sequence being present in multiple copies per cell comprising mtDNA, rDNA, SINE and/or MIR, is greater than or equal to 10 copies (correspondingly approximately 2 fg target sequence to be verified) in the reaction mixture.

CITED LITERATURE

Dolezel J, Bartos J, Voglmayr H, Greilhuber J (2003). Nuclear DNA content and genome size of trout and human. Cytometry A 51:127-8.

Fukuoh A, Cannino G, Gerards M, Buckley S, Kazancioglu S, Scialo F, Lihavainen E, Ribeiro A, Dufour E, Jacobs H T (2014). Screen for mitochondrial DNA copy number maintenance genes reveals essential role for ATP synthase. Mol Syst Biol 10: 734.

Hampl J, Hall M, Mufti N A, Yao Y M, MacQueen D B, Wright W H, Cooper D E (2001). Upconverting phosphor reporters in immunochromatographic assays. Anal Biochem 288:176-187.

Heid C A, Stevens J, Livak K J, Williams P M (1996). Real time quantitative PCR. Genome Res 6, 986-994.

Hirakawa M P, Martinez D A, Sakthikumar S, Anderson M Z, Berlin A, Gujja S, Zeng Q, Zisson E, Wang J M, Greenberg J M, Berman J, Bennett R J, Cuomo C A (2015). Genetic and phenotypic intra-species variation in *Candida albicans*. Genome Res 25: 413-25, Hu J, Wang S, Wang L, Li F, Pingguan-Murphy B, Lu T J, Xu F (2014). Advances in paper-based point-of-care diagnostics, Biosens Bioelectron 54: 585-597.

Kaiser M W, Lyamicheva N, Ma W, Miller C, Neri B, Fors L, Lyamichev V I (1999). A comparison of eubacterial and archaeal structure-specific 5'-exonucleases. J Biol Chem 274: 21387-21394.

Lyamichev V, Brow M A, Dahlberg J E (1993). Structure-specific endonucleolytic cleavage of nucleic acids by eubacterial DNA polymerases, Science 260: 778-783.

MIQ-1 (2011). Mikrobiologisch-infektiologische Qualitatsstandards (MiQ) Nukleinsäure-Amplifikationstechniken (NAT) Richtlinien der DGHM in Zusammenarbeit mit BAMI, DGP, DGPI, DMykG, DSTIG, DTG, DVV, ESGMD/ESCMID, GfV, INSTAND, SGM (Reischl U et al., Urban & Fischer, München, ISBN-13 978-3-437-41535-5).

Rili-BÄK-B3 (2013). Richtlinie der Bundesärztekammer zur Qualitätssicherung laboratoriumsmedizinischer Untersuchungen (Rili-BÄK). Ted B3: Direkter Nachweis and Charakterisierung von Infektionserregem. Deutsches Ärzteblatt 110: A 575-A 582.

Xu Y, Potapova O, Leschziner A E, Grindley N D, Joyce C M (2001). Contacts between the 5' nuclease of DNA polymerase I and its DNA substrate. J Biol Chem 276, 30167-30177.

Zuker M (2003). Mfold web server for nucleic acid folding and hybridization prediction. Nucl Acids Res 31: 3406-3415.

The invention claimed is:

1. A confirmation assay of at least one amplified nucleic acid target sequence (target sequence) during an amplification reaction in a collective and continuous reaction setup containing a reaction mixture comprising:
   at least one target sequence to be verified,
   at least two target sequence-specific primers (P1, P2, $P_{1-n}$) being suitable for amplification of the at least one target sequence,
   at least one labelled target sequence-specific flap endonuclease probe (FEN probe FEN1, $FEN_{1-n}$), wherein the at least one FEN probe comprises
      a target sequence-specific 3'-sequence which is complementary to a sequence fragment of the at least one target sequence within a region being restricted on the target sequence by the at least first primer (P1) and the at least second primer (P2),
      a protective group at the 3'-end of the target sequence-specific 3'-sequence, and
      a target sequence-unspecific 5'-sequence which is labelled at its 5'-end with a first hapten of a specific hapten pair, and
   at least one artificial matrix sequence,
and further wherein per cycle of the amplification reaction, the confirmation assay comprises:
   hybridisation of the target sequence-specific 3'-sequence of the at least one FEN probe to a complementary sequence of the at least one target sequence to be verified,
   cleavage of the at least one FEN probe,
   obtaining of at least one free 5'-cleavage product ($S_{1-n}$) each comprising the target sequence-unspecific 5'-sequence,
   hybridisation of the at least one 5'-cleavage product ($S_{1-n}$) of the at least one FEN probe to a complementary sequence of the at least one artificial matrix sequence,
   amplification of the at least one artificial matrix sequence using the at least one 5'-cleavage product ($S_{1-n}$) of the at least one FEN probe, and
   optionally, labelling of the at least one artificial matrix sequence during amplification by the at least one 5'-cleavage product ($S_{1-n}$) of the at least one FEN probe.

2. The confirmation assay of claim 1, wherein the 5'-end of the target sequence-unspecific 5'-sequence of the at least one FEN probe is labelled with a detector hapten or one hapten of a specific hapten pair being sequence-specific to the matrix sequence.

3. The confirmation assay of claim 1, wherein the at least one target sequence to be verified is present in greater than or equal to 2 copies in the reaction mixture.

4. The confirmation assay of claim 1, wherein the reaction mixture comprises:
   at least two labelled FEN probes (FEN1 and FEN2, $FEN_{1-n}$), each comprising a target sequence-specific 3'-sequence, and/or
   at least one further labelled primer (M1) being complementary to a sequence fragment of a counter strand of the at least one artificial matrix sequence.

5. The confirmation assay of claim 4, wherein a second hapten of the specific hapten pair is present as a label at the 5'-end of the target sequence-unspecific 5'-sequence of a second labelled FEN probe of the at least two labelled FEN probes or of the at least one further primer (M1).

6. The confirmation assay of claim 5, wherein:
   the amplification of the at least one artificial matrix sequence is carried out using at least one labelled 5'-cleavage product ($S_{1-n}$) of the at least one FEN probe and at least one further labelled 5'-cleavage product of the second FEN probe or of at least one further labelled primer (M1),
   the labelling of the at least one artificial matrix sequence with the specific hapten pair is carried out during amplification to produce at least one hapten pair-labelled artificial matrix sequence amplification product, and
   at least one labelled double strand of the at least one matrix sequence amplification product having one hapten of the specific hapten pair at the respective strand is obtained.

7. The conformation assay of claim 6, wherein the confirmation of the at least one amplified target sequence to be verified is the at least one hapten pair-labelled artificial matrix sequence amplification product.

8. The confirmation assay of claim 6, wherein the at least one hapten pair-labelled artificial matrix sequence amplification product is detected via an immunochromatographic method.

9. The confirmation assay of claim 6, wherein the at least one hapten pair-labelled artificial matrix sequence amplification product is detected via a nucleic acid lateral flow (NALF) immunochromatographic method.

10. The confirmation assay of claim 6, further comprising adding a suitable buffer to the at least one hapten pair-labelled artificial matrix sequence amplification product, and immediately supplying the mixture to an immunochromatographic method.

11. The confirmation assay of claim 1, wherein the reaction mixture further comprises at least one enzyme being suitable for cleavage of the at least one FEN probe, which is selected from a FEN as intrinsic component of a DNA polymerase or as enzyme separated from a polymerase.

12. The confirmation assay of claim 1, wherein the reaction mixture further comprises at least one FEN enhancer oligonucleotide ($ENH_{1-n}$), the sequence of which at the 3'-end overlaps by at least one base with the target sequence-specific 3'-sequence at the 5'-binding site of the at least one FEN probe.

13. The confirmation assay of claim 1, wherein the reaction mixture comprises at least two artificial matrix sequences differing in sequence and/or in sequence length and each comprising complementary sequences to at least one 5'-cleavage product ($S_{1-n}$) of the respective FEN probe or to at least one further primer (M1).

14. The confirmation assay of claim 1, wherein the reaction mixture comprises:
   2 to 10 different FEN probes, each labelled with one hapten of the 2 to 10 different specific hapten pairs, and
   2 to 10 different artificial matrix sequences, each comprising a sequence fragment that is complementary to a labelled 5'-cleavage product ($S_{1-n}$) of a FEN probe.

15. The confirmation assay of claim 14, wherein the 2 to 10 different artificial matrix sequence amplification products labelled with one specific hapten pair each are confirmed in a collective and continuous reaction, and are simultaneously and distinctly detected at a solid phase via an immunochromatographic method.

16. A multiplex kit comprising:
   at least two target sequence-specific primers (P1, P2, $P_{1-n}$), wherein the at least two target sequence-specific primers are suitable for amplification of at least one pre-determined target sequence of a DNA probe of a patient to be verified, at least one labelled or more labelled target sequence-specific flap endonuclease (FEN) probe (FEN1, $FEN_{1-n}$) differing from one another, and each FEN probe respectively comprises:
- a pre-determined target sequence-specific 3'-sequence of a DNA probe of a patient which is complementary to a sequence fragment of the at least one pre-determined target sequence within a region being restricted on the target sequence by the at least first primer (P1) and the at least second primer (P2),
- a protective group at the 3'-end of the pre-determined target sequence-specific 3'-sequence, and
- a pre-determined target sequence-unspecific 5'-sequence which is labelled at its 5'-end with a detector hapten or one hapten of a specific hapten pair being sequence-specific to the matrix sequence, and at least one or more different artificial matrix sequences differing in their sequence and/or in their sequence length and each comprising complementary sequences to at least one 5' cleavage product ($S_{1-n}$) of the respective FEN probe or to at least one further primer (M1).

17. The multiplex kit of claim 16, comprising:
- at least one further labelled primer (M1) that is complementary to a sequence fragment of a counter strand of the at least one artificial matrix sequence, and/or
- at least one FEN enhancer oligonucleotide ($ENH_{1-n}$), the sequence of which at the 3'-end overlaps by at least one base with the target sequence-specific 3'-sequence at the 5'-binding site of the at least one FEN probe.

18. The multiplex kit of claim 16, wherein a second hapten of the specific hapten pair is present as a label at the 5'-end of the target sequence-unspecific 5'-sequence of the at least second FEN probe (FEN1, FEN2, $FEN_{1-n}$) or at the at least one further primer (M1).

* * * * *